US008580272B2

(12) United States Patent
Liu et al.

(10) Patent No.: US 8,580,272 B2
(45) Date of Patent: Nov. 12, 2013

(54) **COMPOSITIONS AND METHODS FOR DETECTION OF ANTIBODIES SPECIFIC FOR *ANAPLASMA PHAGOCYTOPHILUM* (APH) AND *ANAPLASMA PLATYS* (APL)**

(71) Applicant: IDEXX Laboratories, Inc., Westbrook, ME (US)

(72) Inventors: Jiayou Liu, Scarborough, ME (US); Eugene Regis Krah, III, Freeport, ME (US); Thomas Patrick O'Connor, Jr., Westbrook, ME (US); Daniel Karl Rieger, Cape Elizabeth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

(21) Appl. No.: 13/668,597

(22) Filed: Nov. 5, 2012

(65) Prior Publication Data

US 2013/0064842 A1 Mar. 14, 2013

Related U.S. Application Data

(62) Division of application No. 12/575,531, filed on Oct. 8, 2009, now Pat. No. 8,303,959.

(60) Provisional application No. 61/103,743, filed on Oct. 8, 2008.

(51) Int. Cl.
 *A61K 39/02* (2006.01)
 *G01N 33/569* (2006.01)

(52) U.S. Cl.
 USPC ............... 424/190.1; 424/234.1; 435/7.1

(58) Field of Classification Search
 None
 See application file for complete search history.

(56) References Cited

U.S. PATENT DOCUMENTS

| | | | |
|---|---|---|---|
| 5,192,679 A | 3/1993 | Dawson |
| 5,401,656 A | 3/1995 | Dawson |
| 5,413,931 A | 5/1995 | Dawson |
| 5,726,010 A | 3/1998 | Clark |
| 5,789,176 A | 8/1998 | Dawson |
| 5,869,335 A | 2/1999 | Munderloh |
| 5,928,879 A | 7/1999 | Dumler |
| 5,955,359 A | 9/1999 | Dumler |
| 5,976,791 A | 11/1999 | Mabilat |
| 5,976,860 A | 11/1999 | Coughlin |
| 5,989,848 A | 11/1999 | Dawson |
| 6,015,691 A | 1/2000 | Walker |
| 6,025,338 A | 2/2000 | Barbet |
| 6,034,085 A | 3/2000 | Joshi |
| 6,204,252 B1 | 3/2001 | Murphy |
| 6,207,169 B1 | 3/2001 | Reed |
| 6,231,869 B1 | 5/2001 | Reed |
| 6,277,381 B1 | 8/2001 | Reed |
| 6,284,238 B1 | 9/2001 | Coughlin |
| 6,306,394 B1 | 10/2001 | Murphy |
| 6,306,402 B1 | 10/2001 | Reed |
| 6,355,777 B1 | 3/2002 | Walker |
| 6,392,023 B1 | 5/2002 | Walker |
| 6,403,780 B1 | 6/2002 | Walker |
| 6,458,942 B1 | 10/2002 | Walker |
| 6,964,855 B2 | 11/2005 | O'Connor, Jr. |
| 7,439,321 B2 | 10/2008 | O'Connor, Jr. |
| 2002/0064531 A1 | 5/2002 | Walker |
| 2002/0064535 A1 | 5/2002 | Reed |
| 2002/0068343 A1 | 6/2002 | Reed |
| 2002/0086984 A1 | 7/2002 | Reed |
| 2002/0115840 A1 | 8/2002 | Walker |
| 2002/0132789 A1 | 9/2002 | Barbet |
| 2003/0099639 A1 | 5/2003 | Rikihisa |
| 2005/0124015 A1 | 6/2005 | O'Connor, Jr. |
| 2005/0142557 A1 | 6/2005 | Alleman |
| 2008/0248497 A1 | 10/2008 | Beall |
| 2009/0042222 A1 | 2/2009 | O'Connor, Jr. et al. |

FOREIGN PATENT DOCUMENTS

| | | |
|---|---|---|
| WO | 98/42740 | 1/1998 |
| WO | 98/49313 | 11/1998 |
| WO | 99/13720 | 3/1999 |
| WO | 99/52370 | 10/1999 |
| WO | 01/85949 | 11/2001 |
| WO | WO 03087757 A2 * | 10/2003 |
| WO | 2009/070507 | 4/2009 |

OTHER PUBLICATIONS

McBride et al., "Molecular Cloning of the Gene for a Conserved Major Immunoreactive 28-Kilodalton Protein of *Ehrlichia canis*: a Potential Serodiagnostic Antigen", Clinical and Diagnostic Laboratory Immunology, 6:392-399 (1999).

McBride et al., "A Conserved, Transcriptionally Action p28 Multigene Locus of *Ehrlichia canis*", Gene, 254:245-252 (2000).

Murphy et al., "Major antigenic proteins of the agent of human granulocytic ehrlichiosis are encoded by members of a multigene family", Infection and Immunity, 66(8):3711-3781 (1998).

Ohashi et al., "Cloning and Characterization of Multigenes Encoding the Immunodominant 30-Kilodalton Major Outer Membrane Proteins of *Ehrlichia canis* and Application of the Recombinant Protein for Serodiagnosis", Journal of Clinical Microbiology, 36:2671-2680 (1998).

Ohashi et al., "Immunodominant Major Outer Membrane Proteins of *Ehrlichia chaffeensis* are Encoded by a Polymorphic Multigene Family", Infection and Immunity, 66:132-139 (1998).

Suksawat et al., "Seroprevalence of *Ehrlichia canis, Ehrlichia equi* and *Ehrlichia risticii* in Sick Dogs from North Carolina and Virginia", Journal. Vet. Internal. Med., 14:50 (2000).

Yu et al., "Comparison of *Ehrlichia chaffeensis* Recombinant Proteins for Serlogic Diagnosis of Human Monocytotropic Ehrlichiosis", Journal of Clinical Microbiology, 37:2568-2575 (1999).

(Continued)

*Primary Examiner* — Brian J Gangle
(74) *Attorney, Agent, or Firm* — McDonnell Boehnen Hulbert & Berghoff LLP

(57) ABSTRACT

The invention provides methods and compositions for the detection and treatment of *Anaplasma phagocytophilum* and *Anaplasma platys* infection.

10 Claims, 6 Drawing Sheets

(56) References Cited

OTHER PUBLICATIONS

Yu et al., "Genetic Diversity of the 28-Kilodalton Outer Membrane Protein Gene in Human Isolates of *Ehrlichia chaffeensis*", Journal of Clinical Microbiology, 37:1137-1143 (1999).

Yu et al., "Characterization of the Complete Transcriptionally Active *Ehrlichia chaffeensis* 28 kDa Outer Membrane Protein Multigene Family", Gene, 248:59-68 (2000).

Asanovich et al., "Particial characterization of Cloned Genes Encoding Immunoreactive Proteins of *Ehrlichia equi* and the Agent of Human Granulocytic Ehrlichiosis", Ab. Gen. Meet. American Society of Microbiology, Abstract No. D-22, p. 245 (1996).

Lodes et al., "Serodiagnosis of Human Granulocytic Ehrlichiosis by using Novel Combinations of Immunoreactive Recombinant Proteins", Journal of Clinical Microbiology, 39(7):2471-2473 (2001).

Wormser et al., "False-Positive Lyme Disease Serology in Human Granulocytic Ehrlichiosis", Lancet, 347:981-982 (1996).

Magnarelli et al., "Coexistence of Antibodies to Tick-Borne Pathogens of Babesiosis, Ehrlichiosis, and Lyme Borreliosis in Human Sera", Journal of Clinical Microbiology, 33(1):3054-3057 (1995).

"Notification List—Notification that new names and new combinations have appeared in vol. 51, part 6, of the IJSEM", International Journal of Systematic and Evolutionary Microbiology, 52:5-6 (2002).

International Search Report dated Sep. 17, 2003, for PCT/US03/10131.

Communication for corresponding European application No. 03719550.0-2401, PCT/US03/10131 dated Apr. 21, 2006.

Greenspan et al., "Defining Epitopes: It's Not as Easy as it Seems", Nature Biotech, 17:936-937 (1999).

Bowie et al., "Deciphering the Message in Protein Sequences: Tolerance to Amino Acid Substitutions", Science, 247:1306-1310 (1990).

Blythe et al., "Benchmarking B cell epitope prediction: Underperformance of existing methods", Protein Science, 14:246-248 (2005).

Dunning Hotopp, "Comparative Genomics of Emerging Human Ehrlichiosis Agents", PLoS Genetics, 2(2):0208-0223 (2006).

UniProtKB/TrEMBL Q2GJG3 dated Mar. 21, 2006.

Alta Biosencies, "FAQ Peptides for antibodies", Last Updated Jan. 2010 [Retrieved from the Internet on Jan. 29, 2010: <URL:http://www.altabioscience.bham.ac.uk/services/peptide/antibodies.shtml>]; section 'What is the optimum length of a peptide'.

Ge et al., "Identification of Novel Surface Proteins of Anaplasma phagocytophilum by Affinity Purification and Proteomics", J. Bacteriol., 189(21):7819-7828 (2007).

International Search Report and Written Opinion dated Feb. 24, 2010, for corresponding PCT application No. PCT/US09/59956.

Wang et al. "Two Monoclonal Antibodies with Defined Epitopes of P44 Major Surface Proteins Neutralize Anaplasma phagocytophilum by Distinct Mechanisms", Infection and Immunity, 74(3):1873-1882 (2006).

Sequence alignment, http://blast.ncbi.nlm.nih.gov/Blast.cgi, run on Oct. 20, 2011.

\* cited by examiner

| Sample | Aph rp44 CO=0.13 | Aph p44-4 CO=0.05 | Apl p44-4 CO=0.07 |
|---|---|---|---|
| HP123 | 0.51 | 0.04 | 2.54 |
| HP133 | 0.12 | 0.04 | 3.12 |
| HP135 | 0.29 | 0.04 | 1.84 |
| HP136 | 0.56 | 0.04 | 3.01 |
| HP166 | 0.74 | 0.04 | 2.95 |
| P23 | 1.23 | 0.04 | 0.58 |
| P24 | 0.37 | 0.03 | 2.14 |
| P28 | 0.48 | 0.03 | 0.77 |
| P30 | 0.26 | 0.03 | 1.61 |
| P33 | 0.38 | 0.04 | 0.11 |
| P36 | 0.26 | 0.03 | 1.17 |
| P37 | 0.77 | 0.03 | 0.09 |

Figure 2

| sample | Aph rp44 CO=0.15 | Aph p44-4 CO=0.05 | Apl p44-4 CO=0.07 |
|---|---|---|---|
| ME-580 | 1.27 | 3.87 | 0.04 |
| ME-492 | 2.09 | 3.87 | 0.03 |
| ME-559 | 1.09 | 3.80 | 0.07 |
| ME-494 | 2.53 | 3.76 | 0.04 |
| ME-333 | 2.76 | 3.69 | 0.08 |
| ME-478 | 2.20 | 3.61 | 0.05 |
| ME-583 | 0.70 | 3.37 | 0.10 |
| ME-593 | 1.96 | 3.26 | 0.03 |
| ME-550 | 1.42 | 2.94 | 0.04 |
| ME-579 | 0.58 | 2.29 | 0.09 |
| ME-553 | 1.16 | 1.20 | 0.03 |
| ME-635 | 1.79 | 1.16 | 0.06 |
| ME-582 | 0.12 | 0.55 | 0.05 |
| ME-314 | 0.79 | 0.47 | 0.06 |
| ME-557 | 0.54 | 0.37 | 0.07 |
| ME-566 | 1.45 | 0.28 | 0.05 |
| ME-552 | 0.73 | 0.24 | 0.05 |
| ME-620 | 0.73 | 0.16 | 0.05 |
| ME-568 | 1.04 | 0.16 | 0.03 |
| ME-555 | 0.45 | 0.13 | 0.03 |
| ME-564 | 0.60 | 0.05 | 0.08 |
| ME-581 | 2.11 | 0.05 | 0.03 |

Figure 3

| Canine ID | Days PI | Aph rp44 CO=0.13 | Aph p44-4 CO=0.05 | Apl p44-4 CO=0.07 |
|---|---|---|---|---|
| 280610 | 3 | 0.09 | 0.05 | 0.03 |
| | 7 | 0.07 | 0.04 | 0.04 |
| | 10 | 0.17 | 0.04 | 2.08 |
| | 14 | 1.07 | 0.04 | 3.94 |
| | 17 | 0.65 | 0.04 | 3.37 |
| | 21 | 0.23 | 0.03 | 2.28 |
| | 24 | 0.14 | 0.03 | 1.80 |
| | 28 | 0.27 | 0.03 | 1.43 |
| | 35 | 0.16 | 0.04 | 1.12 |
| | 42 | 0.70 | 0.04 | 0.38 |
| | 49 | 0.56 | 0.03 | 0.24 |
| | 56 | 0.38 | 0.04 | 0.13 |
| | 63 | 0.25 | 0.04 | 0.11 |
| | 71 | 0.22 | 0.04 | 0.10 |

Figure 4

Canine 07-041

| DPI | Aph rp44 CO=0.15 | Aph p44-4 CO=0.05 |
|---|---|---|
| 0 | 0.04 | 0.04 |
| 2 | 0.04 | 0.04 |
| 4 | 0.05 | 0.04 |
| 7 | 0.09 | 0.03 |
| 10 | 0.46 | 0.04 |
| 14 | 2.55 | 0.25 |
| 17 | 2.21 | 0.22 |
| 21 | 2.18 | 0.17 |
| 24 | 1.45 | 0.15 |
| 30 | 1.34 | 0.12 |
| 45 | 2.08 | 0.42 |
| 54 | 2.37 | 0.86 |
| 60 | 2.97 | 1.54 |

Canine 07-044

| DPI | Aph rp44 CO=0.15 | Aph p44-4 CO=0.05 |
|---|---|---|
| 0 | 0.04 | 0.03 |
| 2 | 0.04 | 0.03 |
| 4 | 0.04 | 0.04 |
| 7 | 0.06 | 0.04 |
| 10 | 2.07 | 0.34 |
| 14 | 2.14 | 0.95 |
| 17 | 2.31 | 1.27 |
| 21 | 2.18 | 0.71 |
| 24 | 1.70 | 0.96 |
| 30 | 1.29 | 0.70 |
| 45 | 1.67 | 0.92 |
| 54 | 1.78 | 1.20 |
| 60 | 1.94 | 1.21 |

Canine 07-042

| DPI | Aph rp44 CO=0.15 | Aph p44-4 CO=0.05 |
|---|---|---|
| 0 | 0.23 | 0.04 |
| 2 | 0.21 | 0.05 |
| 4 | 0.21 | 0.05 |
| 7 | 0.22 | 0.04 |
| 10 | 1.83 | 0.22 |
| 14 | 2.40 | 1.37 |
| 17 | 2.24 | 1.13 |
| 21 | 2.29 | 0.68 |
| 24 | 1.97 | 0.39 |
| 30 | 2.45 | 0.50 |
| 45 | 2.65 | 1.18 |
| 54 | 2.90 | 1.51 |
| 60 | 2.84 | 1.41 |

Canine 07-045

| DPI | Aph rp44 CO=0.15 | Aph p44-4 CO=0.05 |
|---|---|---|
| 0 | 0.05 | 0.04 |
| 2 | 0.04 | 0.04 |
| 4 | 0.18 | 0.05 |
| 7 | 0.13 | 0.04 |
| 10 | 0.43 | 0.04 |
| 14 | 2.49 | 0.16 |
| 17 | 2.40 | 0.33 |
| 21 | 2.31 | 0.30 |
| 24 | 2.20 | 0.30 |
| 30 | 2.16 | 0.45 |
| 45 | 2.06 | 0.30 |
| 54 | 1.92 | 0.56 |
| 60 | 2.01 | 0.75 |

Canine 07-043

| DPI | Aph rp44 CO=0.15 | Aph p44-4 CO=0.05 |
|---|---|---|
| 0 | 0.04 | 0.04 |
| 2 | 0.04 | 0.03 |
| 4 | 0.05 | 0.04 |
| 7 | 0.04 | 0.03 |
| 10 | 0.60 | 0.12 |
| 14 | 1.76 | 0.86 |
| 17 | 2.01 | 2.05 |
| 21 | 1.68 | 1.11 |
| 24 | 1.45 | 0.69 |
| 30 | 1.86 | 0.59 |
| 45 | 1.89 | 0.29 |
| 54 | 1.47 | 0.24 |
| 60 | 1.20 | 0.21 |

Canine 07-046

| DPI | Aph rp44 CO=0.15 | Aph p44-4 CO=0.05 |
|---|---|---|
| 0 | 0.05 | 0.04 |
| 2 | 0.05 | 0.05 |
| 4 | 0.23 | 0.05 |
| 7 | 0.05 | 0.04 |
| 10 | 0.67 | 0.06 |
| 14 | 2.46 | 1.30 |
| 17 | 2.34 | 1.77 |
| 21 | 1.83 | 1.56 |
| 24 | 1.93 | 1.40 |
| 30 | 1.72 | 0.91 |
| 45 | 2.04 | 1.59 |
| 54 | 2.00 | 1.48 |
| 60 | 1.86 | 1.06 |

Figure 5

|  | 0.5 ug/mL coat | | | | | | 1 ug/mL coat | | | | | |
| --- | --- | --- | --- | --- | --- | --- | --- | --- | --- | --- | --- | --- |
|  | VML8 | VML14 | VML21 | VML156 | - | + | VML8 | VML14 | VML21 | VML156 | - | + |
| p44-1 | 0.24 | 0.26 | 0.25 | 0.16 | 0.28 | 1.34 | 0.20 | 0.25 | 0.25 | 0.17 | 0.31 | 1.28 |
| p44-2 | 0.20 | 0.18 | 0.20 | 0.18 | 0.22 | 3.29 | 0.20 | 0.20 | 0.25 | 0.20 | 0.28 | 3.43 |
| p44-3 | 0.37 | 0.41 | 0.49 | 0.25 | 0.24 | 2.46 | 0.36 | 0.38 | 0.47 | 0.28 | 0.30 | 2.69 |
| p44-4 | 1.30 | 1.92 | 2.99 | 0.84 | 0.18 | 3.33 | 1.19 | 1.73 | 2.76 | 0.79 | 0.20 | 3.44 |

Figure 6

COMPOSITIONS AND METHODS FOR DETECTION OF ANTIBODIES SPECIFIC FOR *ANAPLASMA PHAGOCYTOPHILUM* (APH) AND *ANAPLASMA PLATYS* (APL)

PRIORITY

This application is a divisional application of U.S. Ser. No. 12/575,531, filed Oct. 8, 2009, now U.S. Pat. No. 8,303,959, which claims the benefit of U.S. application 61/103,743, filed Oct. 8, 2008. These applications are incorporated herein by reference in their entirety.

SEQUENCE LISTING

This document incorporates by reference an electronic sequence listing text file, which was electronically submitted along with this document. The text file is named 08_1241_SeqListing_ST25_2.txt, is 12,100 bytes, and was created on Nov. 5, 2012.

BACKGROUND OF THE INVENTION

Anaplasmosis occurs in mammals, including, e.g., humans, horses, sheep, dogs, cats, deer, and ruminants and is caused by infection of granulocytic cells with the tick-borne agent *Anaplasma phagocytophilum* ("Aph") (formerly known as *Ehrlichia equi*). Common clinical symptoms include fever, lethargy, lameness, thrombocytopenia, swelling of the lymph nodes, and anexoria, all of which are non-specific to anaplasmosis. Therefore a specific test is important for correct diagnosis.

*Anaplasma platys* ("Apl") (formerly known as *Ehrlichia platys*) is a very closely related species. Apl can cause infectious canine cyclic thrombocytopenia (ICCT). Infected dogs are usually asymptomatic in the U.S.A, but may become clinically ill in other parts of the world. Current serologic tests for *Anaplasma* can not differentiate the two species because of significant cross-reactivity. Methods of detecting Aph and Apl and methods of differentiating between the two infections are needed in the art.

The onset of clinical symptoms occurs during the acute phase of anaplasmosis can precede the advent of measurable levels of antibodies against some *Anaplasma* antigens. Thus, there is a need for a rapid, sensitive and reliable immunological test for Aph infection, Apl infection, or both, e.g., in mammals exhibiting clinical symptoms of acute anaplasmosis.

SUMMARY OF THE INVENTION

One embodiment of the invention provides a composition comprising one or more purified polypeptides consisting of an amino acid sequence set forth as SEQ ID NO:8 or SEQ ID NO:10; or consisting of: amino acids 1 to 45 of SEQ ID NO:10; amino acids 41 to 89 of SEQ ID NO:10; amino acids 85 to 130 of SEQ ID NO:10; amino acids 126 to 160 of SEQ ID NO:10; amino acids 129 to 146 of SEQ ID NO:10; amino acids 144 to 160 of SEQ ID NO:10; or amino acids 136 to 155 of SEQ ID NO:10; or consisting of at least 17 contiguous amino acids of an amino acid sequence set forth as SEQ ID NOs:1-21; or consisting of a polypeptide having at least about 94% identity to SEQ ID NOs:1-21. The one or more purified polypeptides can be linked to an indicator reagent, a signal sequence, a stop transfer sequence, an amino acid spacer, a transmembrane domain, a protein purification ligand, a heterologous polypeptide, a moiety that enhances an immune response, a moiety that facilitates purification, a moiety that facilitates polypeptide stability, one or more additional polypeptides comprising SEQ ID NOs:1-21 or a combination thereof. Another embodiment of the invention provides an isolated polynucleotide that encodes the one or more of the purified polypeptides.

Yet another embodiment of the invention provides a method of detecting antibodies that specifically bind an *Anaplasma phagocytophilum* polypeptide or an *Anaplasma platys* polypeptide or both in a test sample. The method comprises contacting the composition comprising one or more purified polypeptides with the test sample, under conditions that allow polypeptide/antibody complexes to form. The polypeptide/antibody complexes are detected. The detection of the polypeptide/antibody complexes is an indication that antibodies specific for an *Anaplasma phagocytophilum* polypeptide or an *Anaplasma platys* polypeptide or both are present in the test sample. The composition comprising one of more purified polypeptides can consist of at least 17 contiguous amino acids of an amino acid sequence set forth as SEQ ID NOs:8 or 19. The detection of the polypeptide/antibody complexes is an indication that antibodies specific for *Anaplasma platys* are present in the test sample. The composition comprising one or more purified polypeptides can consist of at least 17 contiguous amino acids of an amino acid sequence set forth as SEQ ID NO:10; amino acids 41-89 of SEQ ID NO:10; or amino acids 85-130 of SEQ ID NO:10; or can consist of a polypeptide having at least about 94% identity to SEQ ID NOs:10, amino acids 41-89 of SEQ ID NO:10, or amino acids 85-130 of SEQ ID NO:10. The detection of the polypeptide/antibody complexes is an indication that antibodies specific for an *Anaplasma phagocytophilum* polypeptide or an *Anaplasma platys* polypeptide or both are present in the test sample. The composition comprising one of more purified polypeptides can consist of at least 17 contiguous amino acids of amino acids 1-45 of SEQ ID NO:10; amino acids 126-160 of SEQ ID NO:10; amino acids 129-146 of SEQ ID NO:10; amino acids 144-160 of SEQ ID NO:10; amino acids 136-155 of SEQ ID NO:10; or can consist of a polypeptide having at least about 94% identity to amino acids 1-45 of SEQ ID NO:10; amino acids 126-160 of SEQ ID NO:10; amino acids 129-146 of SEQ ID NO:10; amino acids 144-160 of SEQ ID NO:10; amino acids 136-155 of SEQ ID NO:10. The detection of the polypeptide/antibody complexes is an indication that antibodies specific for an *Anaplasma phagocytophilum* polypeptide are present in the test sample. The complexes can be contacted with an indicator reagent prior to the detection. The amount of antibodies in the test sample can be determined. The one or more purified polypeptides can be attached to a substrate.

Still another embodiment of the invention provides an antibody that specifically binds to a polypeptide consisting of SEQ ID NOs:1-21. The antibody can be a monoclonal antibody, polyclonal antibody, a Fab fragment, a Fab' fragment, Fab'-SH fragment, F(ab')$_2$ fragment, Fv fragment, or a single chain antibody.

Even another embodiment of the invention provides a method of detecting an *Anaplasma phagocytophilum* polypeptide or an *Anaplasma platys* polypeptide or both in a sample. The method comprises contacting one or more antibodies that specifically bind to the one or more purified polypeptides of the invention with the sample under conditions that allow polypeptide/antibody complexes to form. The polypeptide/antibody complexes are detected. The detection of the polypeptide/antibody complexes is an indication that an *Anaplasma phagocytophilum* polypeptide or an *Anaplasma platys* polypeptide or both is present in the sample.

The one or more purified polypeptides can consist of at least 17 contiguous amino acids of amino acids 1-45 of SEQ ID NO:10, amino acids 126-160 of SEQ ID NO:10; amino acids 129-146 of SEQ ID NO:10; amino acids 144-160 of SEQ ID NO:10; or amino acids 136-155 of SEQ ID NO:10. The detection of the polypeptide/antibody complexes is an indication that *Anaplasma phagocytophilum* polypeptides are present in the test sample. The one or more purified polypeptides can consist of at least 17 contiguous amino acids of an amino acid sequence set forth as SEQ ID NOs:8 or 19. The detection of the polypeptide/antibody complexes is an indication that *Anaplasma platys* polypeptides are present in the test sample. The one or more purified polypeptides can consist of at least 17 contiguous amino acids of an amino acid sequence set forth as SEQ ID NOs:10; amino acids 41-89 of SEQ ID NO:10; or amino acids 85-130 of SEQ ID NO:10. The detection of the polypeptide/antibody complexes is an indication that an *Anaplasma phagocytophilum* polypeptide or an *Anaplasma platys* polypeptide is present in the test sample. The one or more antibodies can be monoclonal antibodies, polyclonal antibodies, Fab fragments, Fab' fragments, Fab'-SH fragments, F(ab')$_2$ fragments, Fv fragments, or single chain antibodies.

In another embodiment of the invention, a composition comprising purified polypeptides of the invention further comprises a pharmaceutically-acceptable or veterinarily acceptable carrier and/or an adjuvant.

Yet another embodiment of the invention provides a method of treating or ameliorating *Anaplasma platys* infection, *Anaplasma phagocytophilum* infection, or both, in a mammalian subject comprising administering to the mammalian subject a therapeutically effective amount of a composition comprising one or more of the purified polypeptides of the invention.

Even another embodiment of the invention provides a method of inducing an immune response in a mammal comprising administering an immunologically effective amount of a composition comprising one or more of the purified polypeptides of the invention.

The invention therefore provides methods and compositions for the detection and treatment of Apl and/or Aph infection.

BRIEF DESCRIPTION OF THE DRAWINGS

FIG. 2 shows the results of assays completed with polypeptides comprising SEQ ID NOs:15, 19, and 10.

FIG. 3 shows the results of assays completed with polypeptides comprising SEQ ID NOs:15, 19, and 10.

FIG. 4 shows the results of time course assays completed with polypeptides comprising SEQ ID NOs:15, 19, and 10.

FIG. 5 shows the results of time course assays completed with polypeptides comprising SEQ ID NOs:15 and 10.

FIG. 6 shows the results of assays completed with polypeptides comprising SEQ ID NOs:12-15.

DETAILED DESCRIPTION OF THE INVENTION

Polypeptides of the Invention

Figure 1:
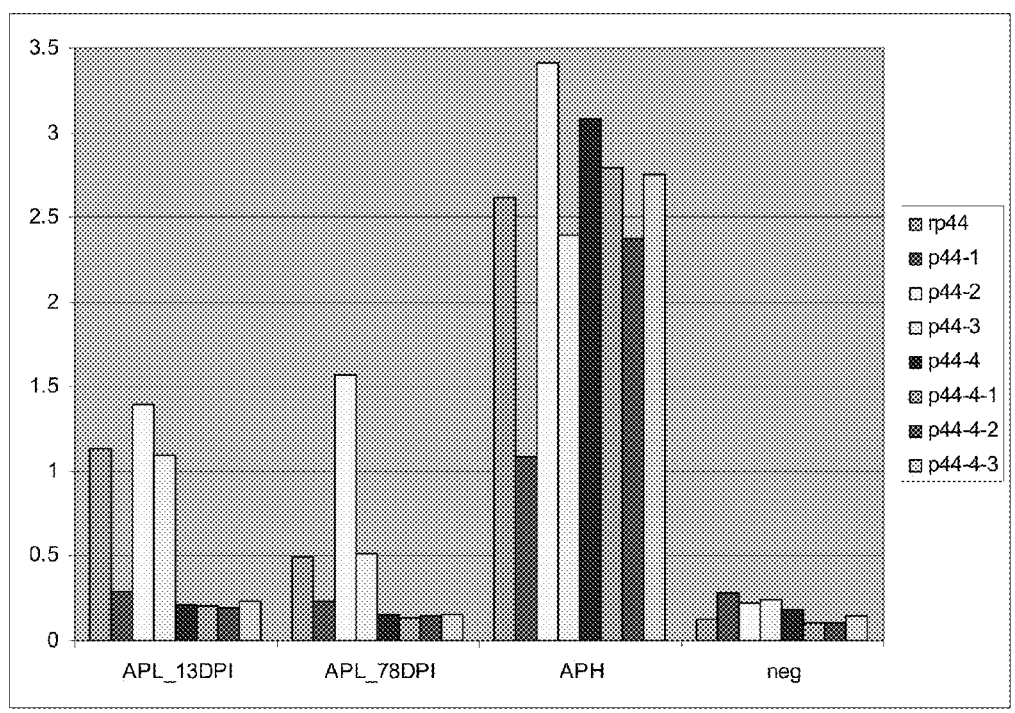
FIG. 1 shows the results of assays completed with polypeptides comprising SEQ ID NOs:12-18 and 10.

As used herein, the singular forms "a," "an", and "the" include plural referents unless the context clearly dictates otherwise.

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

One embodiment of the invention provides one or more of the following polypeptides:

| | |
|---|---|
| Aph p44-1 | GSDVRAHDDVSALETGGAGYFYVGLDYSPAFSKIRDFS IRESNGE 45 (SEQ ID NO: 1) |
| Aph p44-2 | ESNGETKAVYPYLKDGKSVKLESHKFDWNTPDPRIGFK DNMLVAMEGSV 49 (SEQ ID NO: 2) |
| Aph p44-3 | MEGSVGYGIGGARVELEIGYERFKTKGIRDSGSKEDEA DTVYLLAK 46 (SEQ ID NO: 3) |
| Aph p44-4 | YLLAKELAYDVVTGQTDNLAAALAKTSGKDIVQFA 35 (SEQ ID NO: 4) |
| Aph p44-4-1 | AKELAYDVVTGQTDNLAA 18 (SEQ ID NO: 5) |
| Aph p44-4-2 | LAAALAKTSGKDIVQFA 17 (SEQ ID NO: 6) |
| Aph p44-4-3 | VVTGQTDNLAAALAKTSGKD 20 (SEQ ID NO: 7) |
| Apl p44-4 | AKKLPHTLVSDQSDKFLEELKNTKAAEIVKFA 32 (SEQ ID NO: 8) |
| p44-4-V | YLLAKELAYDVVTGQTDKLTAALAKTSGKDFVQFA 35 (SEQ ID NO: 9) |
| Aph rp44 | GSDVRAHDDVSALETGGAGYFYVGLDYSPAFSKIRDFSIRESNGETKAVY PYLKDGKSVKLESHKFDWNTPDPRIGFKDNMLVAMEGSVGYGIGGARVEL EIGYERFKTKGIRDSGSKEDEADTVYLLAKELAYDVVTGQTDXLXAALAK TSGKDXVQFANAVKISSPTIDGKVCSGDHAAIVSTKGKDYKADPKESGNN GHETSQCSGLSSS 213 (SEQ ID NO: 10) |

In one embodiment of the invention, the X at position 143 of SEQ ID NO:10 is K or N; the X at position 145 is T or A; and the X at position 156 is F or I.

One embodiment of the invention provides the following polypeptides:
1. Amino acids 1-45 of SEQ ID NO:10 (Aph p44-1) (which has the same reactivities of SEQ ID NOs:1 and 12).
2. Amino acids 41-89 of SEQ ID NO:10 (Aph p44-2) (which has the same reactivities of SEQ ID NOs:2 and 13).
3. Amino acids 85-130 of SEQ ID NO:10 (Aph p44-3) (which has the same reactivities of SEQ ID NOs:3 and 14).

4. Amino acids 126-160 of SEQ ID NO:10 (Aph p44-4) (which has the same reactivities of SEQ ID NOs:4, 9, 11, 15, and 20).
5. Amino acids 129-146 of SEQ ID NO:10 (Aph p44-4-1) (which has the same reactivities of SEQ ID NOs:5 and 16).
6. Amino acids 144-160 of SEQ ID NO:10 (Aph p44-4-2) (which has the same reactivities of SEQ ID NOs:6 and 17).
7. Amino acids 136-155 of SEQ ID NO:10 (Aph p44-3) (which has the same reactivities of SEQ ID NOs:7 and 18).

Furthermore, SEQ ID NOs:8 and 9 have the same reactivities, that is, the polypeptides specifically bind antibodies specific for *Anaplasma* antigens in substantially the same manner.

In one embodiment of the invention, the polypeptides have an N-terminal C-residue. For example:

```
Aph p44-1     CGSDVRAHDDVSALETGGAGYFYVGLDYSPAFSKIR
              DFSIRESNGE (SEQ ID NO: 12)

Aph p44-2     CESNGETKAVYPYLKDGKSVKLESHKFDWNTPDPRI
              GFKDNMLVAMEGSV (SEQ ID NO: 13)

Aph p44-3     CMEGSVGYGIGGARVELEIGYERFKTKGIRDSGSKE
              DEADTVYLLAK (SEQ ID NO: 14)

Aph p44-4     CYLLAKELAYDVVTGQTDNLAAALAKTSGKDIVQFA
              (SEQ ID NO: 15)

Aph p44-4-1   CAKELAYDVVTGQTDNLAA
              (SEQ ID NO: 16)

Aph p44-4-2   CLAAALAKTSGKDIVQFA
              (SEQ ID NO: 17)

Aph p44-4-3   CVVTGQTDNLAAALAKTSGKD
              (SEQ ID NO: 18)

Apl p44-4     CAKKLPHTLVSDQSDKFLEELKNTKAAEIVKFA
              (SEQ ID NO: 19)

p44-4-V       CYLLAKELAYDVVTGQTDKLTAALAKTSGKDFVQFA
              (SEQ ID NO: 20)
Aph rp44
CGSDVRAHDDVSALETGGAGYFYVGLDYSPAFSKIRDFSIRESNGET
KAVYPYLKDGKSVKLESHKFDWNTPDPRIGFKDNMLVAMEGSVGYGI
GGARVELEIGYERFKTKGIRDSGSKEDEADTVYLLAKELAYDVVTGQ
TDXLXAALAKTSGKDXVQFANAVKISSPTIDGKVCSGDHAAIVSTKG
KDYKADPKESGNNGHETSQCSGLSSS. (SEQ ID NO: 21)
```

In one embodiment of the invention, the X at position 144 of SEQ ID NO:21 is K or N; the X at position 146 is T or A; and the X at position 157 is F or I.

SEQ ID NOs:4-7 and 9 can be aligned as follows:

```
Aph p44-4    YLLAKELAYDVVTGQTDNLAAALAKTSGKDIVQFA (SEQ ID NO: 4)

Aph p44-4-1     AKELAYDVVTGQTDNLAA              (SEQ ID NO: 5)

Aph p44-4-2                   LAAALAKTSGKDIVQFA (SEQ ID NO: 6)

Aph p44-4-3             VVTGQTDNLAAALAKTSGKD    (SEQ ID NO: 7)

Aph p44-4-v  YLLAKELAYDVVTGQTDKLTAALAKTSGKDFVQFA (SEQ ID NO: 9)
```

A consensus sequence of SEQ ID NOs:4-7 and 9 is shown in SEQ ID NO:11:

SEQ ID NO: 11
YLLAKELAYDVVTGQTDXLXAALAKTSGKDXVQFA

In one embodiment of the invention, the X at position 18 of SEQ ID NO:11 is N or K; the X at position 20 is T or A; and the X at position 31 is F or I. One embodiment of the invention comprises amino acids 4-21 of SEQ ID NO:11; amino acids 19-34 of SEQ ID NO:11; or amino acids 11-30 of SEQ ID NO:11.

One embodiment provides a purified polypeptide that consists of less than about 46, 40, 35, 30, 25, 20, 19, 18, 17, 16, 15, 14, 13, 12, 11, 10, 9, 8, 7, or 6 contiguous amino acids (or any range between about 46 and about 6 amino acids) of SEQ ID NOs:1-9 and 11-21. One embodiment provides a purified polypeptide that consists of more than about 6, 7, 8, 9, 10, 11, 12, 13, 14, 15, 16, 17, 18, 19, 20, 25, 30, 35, 40, or 46 contiguous amino acids (or any range between about 46 and about 6 amino acids) of SEQ ID NOs:1-9 and 11-12. Naturally occurring Aph or Apl amino acids are any polypeptides naturally produced by an Aph or Apl organism. A purified polypeptide can comprise less than a certain number of contiguous naturally occurring *Anaplasma* amino acids (e.g., about less than 200, 175, 150, 125, 100, 75, 50, 45, 40, 35, 30, 25, 20, 19, 18, 17, 16, 15, 14, 13, 12, 11, 10, 9, 8, 7, or 6 amino acids (or any range between about 200 and about 6 amino acids)) of SEQ ID NOs:1-21. That is, the purified polypeptide is smaller than the full length polypeptide. The fact that these polypeptides are smaller than a full length *Anaplasma* polypeptide is important because smaller polypeptides can have greater specificity and/or sensitivity than full length polypeptides in Apl and/or Aph assays. Additionally, these smaller polypeptides can be less expensive to manufacture, and may be obtained at greater purity, than the full length polypeptide.

Another embodiment provides a purified polypeptide that consists of less than about 200, 175, 150, 125, 100, 75, 50, 25, 20, 15, 10, 6 or less contiguous naturally occurring *Anaplasma* amino acids (or any range between about 200 and about 6 amino acids) of SEQ ID NO:10. Another embodiment provides a purified polypeptide that consists of more than about 6, 10, 15, 25, 50, 75, 100, 125, 150, 175, 200 or more contiguous naturally occurring *Anaplasma* amino acids (or any range between about 6 and about 200 amino acids) of SEQ ID NO:10.

Variant polypeptides that are at least about 80, 81, 82, 83, 84, 85, 86, 87, 88, 89, 90, 91, 92, 93, 94, 95, 96, 97, 98, or 99% identical to the polypeptide sequences shown in SEQ ID NOs:1-21 are also polypeptides of the invention. For example, a variant polypeptide of SEQ ID NO:1 can be about at least about 98% (about 1 amino acid change), 96% (about 2 amino acid changes), 93% (about 3 amino acid changes), 91% (about 4 amino acid changes), 89% (about 5 amino acid changes), 87% (about 6 amino acid changes), 84% (about 7 amino acid changes), 82% (about 8 amino acid changes), or 80% (about 9 amino acid changes) identical to SEQ ID NO:1. A variant polypeptide of SEQ ID NO:2 can be about at least 98% (about 1 amino acid change), 96% (about 2 amino acid changes), 94% (about 3 amino acid changes), 92% (about 4 amino acid changes), 90% (about 5 amino acid changes), 88% (about 6 amino acid changes), about 86% (about 7 amino acid changes), 84% (about 8 amino acid changes), 82% (about 9 amino acid changes), or 80% (about 10 amino acid changes) identical to SEQ ID NO:2. A variant polypeptide of SEQ ID NO:3 can be at least about 98% (about 1 amino acid change), 96% (about 2 amino acid changes), 94% (about 3 amino acid changes), 91% (about 4 amino acid changes), 89% (about 5 amino acid changes), 87% (about 6 amino acid changes), 85% (about 7 amino acid changes), 83% (about 8 amino acid changes), or 80% (about 9 amino acid changes) identical to SEQ ID NO:3. A variant polypeptide of SEQ ID NOs:4 and 9 can be about at least 97% (about 1 amino acid change), 94% (about 2 amino acid changes), 91% (about 3 amino acid changes), 89% (about 4 amino acid changes), 86% (about 5 amino acid changes), 83% (about 6 amino acid changes), or 80% (about 7 amino acid changes) identical to SEQ ID NOs:4 and 9. A variant polypeptide of SEQ ID NO:5 can be at least about 94% (about 1 amino acid change), 89% (about 2 amino acid changes), or 83% (about 3 amino acid changes) identical to SEQ ID NO:5. A variant polypeptide of SEQ ID NO:6 can be at least about 94% (about 1 amino acid change), 88% (about 2 amino acid changes), or 82% (about 3 amino acid changes) identical to SEQ ID NO:6. A variant polypeptide of SEQ ID NO:7 can be about at least 95% (about 1 amino acid change), 90% (about 2 amino acid changes), 85% (about 3 amino acid changes) or 80% (about 4 amino acid changes) identical to SEQ ID NO:7. A variant polypeptide of SEQ ID NO:8 can be about at least 97% (about 1 amino acid change), 94% (about 2 amino acid changes), 91% (about 3 amino acid changes), 88% (about 4 amino acid changes), 84% (about 5 amino acid changes), or 81% (about 6 amino acid changes) identical to SEQ ID NO:8.

Variant polypeptides have one or more conservative amino acid variations or other minor modifications and retain biological activity, i.e., are biologically functional equivalents. A biologically active equivalent has substantially equivalent function when compared to the corresponding wild-type polypeptide. In one embodiment of the invention a polypeptide has about 1, 2, 3, 4, 5, 10, 15, 20, 30, 40, 50, or less conservative amino acid substitutions.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.*, 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variant polypeptides can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature, i.e., a heterologous amino acid sequence. A heterologous amino acid sequence can be from a non-*Anaplasma phagocytophilum*, a non-*Anaplasma platys* organism, a synthetic sequence, or an *Anaplasma phagocytophilum* sequence or *Anaplasma platys* sequence not usually located at the carboxy or amino terminus of a polypeptide of the invention. Additionally, a polypeptide can be covalently or non-covalently linked to compounds or molecules other than amino acids such as indicator reagents. A polypeptide can be covalently or non-covalently linked to an amino acid spacer, an amino acid linker, a signal sequence, a stop transfer sequence, a transmembrane domain, a protein purification ligand, or a combination thereof. A polypeptide can also be linked to a moiety (i.e., a functional group that can be a polypeptide or other compound) that enhances an immune response (e.g., cytokines such as IL-2), a moiety that facilitates purification (e.g., affinity tags such as a six-histidine tag, trpE, glutathione, maltose binding protein), or a moiety that facilitates polypeptide stability (e.g., polyethylene glycol; amino terminus protecting groups such as acetyl, propyl, succinyl, benzyl, benzyloxycarbonyl or t-butyloxycarbonyl; carboxyl terminus protecting groups such as amide, methylamide, and ethylamide). In one embodiment of the invention a protein purification ligand can be one or more C amino acid residues at, for example, the amino terminus or carboxy terminus of a polypeptide of the invention. An amino acid spacer is a sequence of amino acids that are not associated with a polypeptide of the invention in nature. An amino acid spacer can comprise about 1, 5, 10, 20, 100, or 1,000 amino acids.

If desired, a polypeptide of the invention can be part of a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and Staphylococcal protein A, or combinations thereof. Other amino acid sequences can be present at the C or N terminus of a polypeptide of the invention to form a fusion protein. More than one polypeptide of the invention can be present in a fusion protein. Fragments of polypeptides of the invention can be present in a fusion protein of the invention. A fusion protein of the invention can comprise one or more polypeptides of the invention, fragments thereof, or combinations thereof.

Polypeptides of the invention can be in a multimeric form. That is, a polypeptide can comprise one or more copies of a polypeptide of the invention or a combination thereof. A multimeric polypeptide can be a multiple antigen peptide (MAP). See e.g., Tam, J. Immunol. Methods, 196:17-32 (1996).

Polypeptides of the invention can comprise an antigenic determinant that is recognized by an antibody specific for *Anaplasma phagocytophilum* or *Anaplasma platys* or both *Anaplasma phagocytophilum* and *Anaplasma platys*. The polypeptide can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span an entire polypeptide sequence, can be prepared by proteolytic cleavage. By starting with, for example, 30-mer polypeptide fragments, each fragment can be tested for the presence of epitopes recognized in an ELISA. For example, in an ELISA assay an *Anaplasma phagocytophilum* polypeptide, such as a 30-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 30-mer to map the epitope of interest.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *Anaplasma* cells.

An immunogenic polypeptide of the invention can comprise an amino acid sequence shown in SEQ ID NOs:1-21 or fragments thereof. An immunogenic polypeptide can elicit antibodies or other immune responses (e.g., T-cell responses of the immune system) that recognize epitopes of a polypeptide having SEQ ID NOs:1-21. An immunogenic polypeptide of the invention can also be a fragment of a polypeptide that has an amino acid sequence shown in SEQ ID NOs:1-21. An immunogenic polypeptide fragment of the invention can be about 6, 7, 8, 9, 10, 11, 12, 13, 14, 15, 16, 17, 18, 19, 20, 25, 30, 40, 50, 60, 70, 80, 90, 100, 125, 150, 175, 200 or more amino acids in length. An immunogenic polypeptide fragment of the invention can be about 200, 175, 150, 125, 100, 90, 80, 70, 60, 50, 40, 30, 25, 20, 19, 18, 17, 16, 15, 14, 13, 12, 11, 10, 9, 8, 7, 6, or less amino acids in length.

*Anaplasma* Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. A nucleic acid molecule existing among hundreds to millions of other nucleic acid molecules within, for example, cDNA or genomic libraries, or gel slices containing a genomic DNA restriction digest are not to be considered a purified polynucleotide. The polynucleotides of the invention encode the polypeptides of the invention described above. In one embodiment of the invention the polynucleotides encode a polypeptide shown in SEQ ID NOs:1-21 or fragments thereof.

Polynucleotides of the invention can consist of less than about 639, 450, 300, 225, 147, 138, 135, 105, 96, 60, 54, 51, 45, 30, 20, 10 or less contiguous, naturally occurring (i.e., Aph or Apl polynucleotides) or non-naturally occurring polynucleotides. Polynucleotides of the invention can consist of greater than about 10, 20, 30, 45, 51, 54, 60, 96, 105, 135, 138, 147, 225, 300, 450, 639 or more contiguous, naturally occurring (i.e., Aph or Apl polynucleotides) or non-naturally occurring polynucleotides. The purified polynucleotides can comprise additional heterologous nucleotides (that is, nucleotides that are not from Aph or Apl) and even additional Aph or Apl nucleotides as long as they do not naturally occur contiguously with the polynucleotides. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and Staphylococcal protein A.

Polynucleotides of the invention can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 85, 90, 91, 92, 9394, 95, 96, 97, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of polynucleotides of the invention that encode biologically functional polypeptides also are polynucleotides of the invention.

Polynucleotides of the invention can be obtained from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Polynucleotides of the invention can be used, for example, as probes or primers, for example, PCR primers, to detect the presence of *Anaplasma* polynucleotides in a test sample, such as a biological sample. Probes are molecules capable of interacting with a target nucleic acid, typically in a sequence specific manner, for example, through hybridization. Primers are a subset of probes that can support an enzymatic manipulation and that can hybridize with a target nucleic acid such that the enzymatic manipulation occurs. A primer can be made from any combination of nucleotides or nucleotide derivatives or analogs available in the art that do not interfere with the enzymatic manipulation.

A probe or primer can be about 6, 7, 8, 9, 10, 11, 12, 13, 14, 15, 16, 17, 18, 19, 20, 25, 30, 40, 50, 60, 70, 80, 90, 100, 125, 150, 175, 200 or more contiguous nucleotides that encode polypeptides of the invention.

The hybridization of nucleic acids is well understood in the art and discussed herein. Typically a probe can be made from any combination of nucleotides or nucleotide derivatives or analogs available in the art. The ability of such probes and primers to specifically hybridize to *Anaplasma phagocytophilum* or *Anaplasma platys* polynucleotide sequences will enable them to be of use in detecting the presence of complementary sequences in a given test sample. Polynucleotide probes and primers of the invention can hybridize to complementary sequences in a test sample such as a biological sample, including saliva, sputum, blood, plasma, serum, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers, are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of Apl or an Apl polynucleotide sequence in the sample.

Antibodies

Antibodies of the invention are antibody molecules that specifically bind to an *Anaplasma phagocytophilum* polypeptide or *Anaplasma platys* polypeptide or variant polypeptide of the invention or fragment thereof. An antibody of the invention can be specific for an Aph polypeptide or Apl polypeptide or a variant polypeptide or a combination thereof, for example, an antibody specific for one or more of SEQ ID NOs:1-21. In another embodiment of the invention an antibody is specific for an *Anaplasma phagocytophilum* polypeptide (e.g., an antibody specific for SEQ ID NOs:1, 4, 5, 6, 7, 9, 11, 12, 15, 16, 17, 18, or 20). In another embodiment of the invention, an antibody is specific for an *Anaplasma platys* polypeptide (e.g., an antibody specific for SEQ ID NOs:8 or 19). In another embodiment of the invention an antibody is specific for both an *Anaplasma phagocytophilum* polypeptide and an *Anaplasma platys* polypeptide (e.g., an antibody specific for SEQ ID NOs:2, 3, 10, 13, 14, or 21). One of skill in the art can easily determine if an antibody is specific for an *Anaplasma phagocytophilum* polypeptide or *Anaplasma platys* polypeptide using assays described herein. An antibody of the invention can be a polyclonal antibody, a monoclonal antibody, a single chain antibody (scFv), or an antigen binding fragment of an antibody. Antigen-binding fragments of antibodies are a portion of an intact antibody comprising the antigen binding site or variable region of an intact antibody, wherein the portion is free of the constant heavy chain domains of the Fc region of the intact antibody. Examples of antigen binding antibody fragments include Fab, Fab', Fab'-SH, F(ab')$_2$ and F$_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, *Methods Mol. Biol.* 80:23-37 (1998); Dean, *Methods Mol. Biol.* 32:361-79 (1994); Baileg, *Methods Mol. Biol.* 32:381-88 (1994); Gullick, *Methods Mol. Biol.* 32:389-99 (1994); Drenckhahn et al. *Methods Cell. Biol.* 37:7-56 (1993); Morrison, *Ann. Rev. Immunol.* 10:239-65 (1992); Wright et al. *Crit. Rev. Immunol.* 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that a first antigen, e.g., an *Anaplasma phagocytophilum* or *Anaplasma platys* polypeptide, recognizes and binds to an antibody of the invention with greater affinity than to other, non-specific molecules. A non-specific molecule is an antigen that shares no common epitope with the first antigen. In a preferred embodiment of the invention a non-specific molecule is not derived from *Anaplasma* sp. An *Anaplasma* sp. is any species of the genus *Anaplasma*. For example, an antibody raised against a first antigen (e.g., a polypeptide) to which it binds more efficiently than to a non-specific antigen can be described as specifically binding to the first antigen. In one embodiment, an antibody or antigen-binding fragment thereof specifically binds to a polypeptide of SEQ ID NOs:1-21 or fragments thereof when it binds with a binding affinity $K_a$ of $10^7$ 1/mol or more. Specific binding can be tested using, for example, an enzyme-linked immunosorbant assay (ELISA), a radioimmunoassay (RIA), or a western blot assay using methodology well known in the art.

Antibodies of the invention include antibodies and antigen binding fragments thereof that (a) compete with a reference antibody for binding to SEQ ID NOs:1-21 or antigen binding fragments thereof; (b) binds to the same epitope of SEQ ID NOs:1-21 or antigen binding fragments thereof as a reference antibody; (c) binds to SEQ ID NOs:1-21 or antigen binding fragments thereof with substantially the same $K_d$ as a reference antibody; and/or (d) binds to SEQ ID NOs:1-21 or fragments thereof with substantially the same off rate as a reference antibody, wherein the reference antibody is an antibody or antigen-binding fragment thereof that specifically binds to a polypeptide of SEQ ID NOs:1-21 or antigen binding fragments thereof with a binding affinity $K_a$ of $10^7$ 1/mol or more.

Additionally, monoclonal antibodies directed against epitopes present on a polypeptide of the invention can also be readily produced. For example, normal B cells from a mammal, such as a mouse, which was immunized with a polypeptide of the invention can be fused with, for example, HAT-sensitive mouse myeloma cells to produce hybridomas. Hybridomas producing *Anaplasma*-specific antibodies can be identified using RIA or ELISA and isolated by cloning in semi-solid agar or by limiting dilution. Clones producing *Anaplasma*-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., *P.N.A.S. U.S.A.* 82:8653 1985; Spria et al., *J. Immunolog. Meth.* 74:307, 1984. Monoclonal antibodies of the invention can also be recombinant monoclonal antibodies. See, e.g., U.S. Pat. Nos. 4,474,893; 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., *Nature* 321:522 (1986); Reichmann et al., *Nature* 332:323 (1988); Presta, *Curr. Op. Struct. Biol.* 2:593 (1992)), caninized, canine, or human antibodies. Human antibodies can be made by, for example, direct immortilization, phage display, transgenic mice, or a Trimera methodology, see e.g., Reisener et al., *Trends Biotechnol.* 16:242-246 (1998).

Antibodies that specifically bind *Anaplasma phagocytophilum* antigens to the exclusion of *Anaplasma platys* antigens (e.g., SEQ ID NOs:1, 4, 5, 6, 7, 9, 11, 12, 15, 16, 17, 18, or 20), are particularly useful for detecting the presence of *Anaplasma phagocytophilum* antigens in a sample, such as a serum, blood, plasma, urine, fecal, tissue, cell, or saliva sample from an *Anaplasma phagocytophilum*-infected animal.

Antibodies that specifically bind *Anaplasma platys* antigens to the exclusion of *Anaplasma phagocytophilum* antigens (e.g., SEQ ID NOs:8 or 19), are particularly useful for detecting the presence of *Anaplasma platys* antigens in a sample, such as a serum, blood, plasma, urine, fecal, tissue, or saliva sample from an *Anaplasma platys*-infected animal.

Antibodies that specifically bind *Anaplasma platys* and *Anaplasma phagocytophilum* antigens (e.g., SEQ ID NOs:2, 3, 10, 13, 14, or 21), are particularly useful for detecting the presence of *Anaplasma platys* and *Anaplasma phagocytophilum* antigens in a sample, such as a serum, blood, plasma, urine, fecal, tissue, or saliva sample from an *Anaplasma platys*-infected or *Anaplasma phagocytophilum*-infected animal.

An immunoassay for an *Anaplasma* antigen can utilize one antibody or several antibodies. An immunoassay for an *Anaplasma* antigen can use, for example, a monoclonal antibody specific for an *Anaplasma* epitope, a combination of monoclonal antibodies specific for epitopes of one *Anaplasma* polypeptide, monoclonal antibodies specific for epitopes of different *Anaplasma* polypeptides, polyclonal antibodies specific for the same *Anaplasma* antigen, polyclonal antibodies specific for different *Anaplasma* antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels. Antibodies of the invention can specifically bind Aph antigens only, Apl antigens only, or Apl antigens and Apl antigens.

Antibodies of the invention or fragments thereof can be bound to a support and used to detect the presence of Apl and/or Aph antigens. Supports include, for example, glass, polystyrene, polypropylene, polyethylene, dextran, nylon, amylases, natural and modified celluloses, polyacrylamides, agaroses and magletite.

Antibodies of the invention can further be used to isolate Apl and/or Aph organisms or antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind *Anaplasma* organisms or *Anaplasma* antigens from a sample, such as a biological sample including saliva, serum, sputum, blood, urine, feces, cerebrospinal fluid, amniotic fluid, wound exudate, or tissue. The bound *Anaplasma* organisms or *Anaplasma* antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by Apl and/or Aph. By measuring the increase or decrease of antibodies specific for Apl, and/or Aph in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Methods of Detection

The methods of the invention can be used to detect antibodies or specific binding fragments thereof specific for *Anaplasma* antigens, Apl antigens, Aph antigens, Apl polynucleotides, Aph polynucleotides or a combination thereof in a test sample, such as a biological sample, an environmental sample, or a laboratory sample. A test sample can potentially comprise Apl polynucleotides, Aph polynucleotides, Apl polypeptides, *Anaplasma* sp. polypeptides, Aph polypeptides, antibodies specific for *Anaplasma* sp., antibodies specific for Apl, and/or antibodies specific for Aph, unrelated polynucleotides, polypeptides, antibodies or antigens, combinations of the above, or none of the above. A biological sample can include, for example, sera, blood, cells, plasma, saliva, urine, feces, or tissue from a mammal such as a horse, cat, dog or human. The test sample can be untreated, precipitated, fractionated, separated, diluted, concentrated, or purified.

In one embodiment methods of the invention comprise contacting one or more polypeptides of the invention with a test sample under conditions that allow polypeptide/antibody complexes, i.e., immunocomplexes, to form. That is, polypeptides of the invention specifically bind to antibodies specific for Apl and/or Aph antigens located in the sample. In one embodiment of the invention one or more polypeptides of the invention (e.g., SEQ ID NOs:1, 4, 5, 6, 7, 9, 11, 12, 15, 16, 17, 18, 20 or fragments thereof) specifically bind to antibodies that are specific for Aph antigens and do not specifically bind to Apl antigens. In another embodiment of the invention one or more polypeptides of the invention (e.g., SEQ ID NOs:2, 3, 10, 13, 14, 21 or fragments thereof) specifically bind to antibodies that are specific for both Aph and Apl antigens. In one embodiment of the invention one or more polypeptides of the invention (e.g., SEQ ID NOs:8, 19 or fragments thereof) specifically bind to antibodies that are specific for Apl antigens and do not specifically bind to Aph antigens. One of skill in the art is familiar with assays and conditions that are used to detect antibody/polypeptide complex binding. The formation of a complex between polypeptides and anti-Apl and/or anti-Aph antibodies in the sample is detected. The formation of antibody/polypeptide complexes is an indication that *Anaplasma phagocytophilum* polypeptides and/or *Anaplasma platys* polypeptides are present in the sample. The lack of detection of the polypeptide/antibody complexes is an indication that an *Anaplasma phagocytophilum* polypeptides and/or *Anaplasma platys* polypeptides are not present in the sample.

Antibodies of the invention can be used in a method of the diagnosis of Apl and/or Aph infection by obtaining a test sample from, e.g., a human or animal suspected of having an Apl and/or Aph infection. The test sample is contacted with antibodies of the invention under conditions enabling the formation of antibody-antigen complexes (i.e., immunocomplexes). One of skill in the art is aware of conditions that enable and are appropriate for formation of antigen/antibody complexes. The amount of antibody-antigen complexes can be determined by methodology known in the art. A level that is higher than that formed in a control sample indicates an Apl, and/or Aph infection. A control sample is a sample that does not comprise any Aph and/or Apl polypeptides or antibodies specific for Aph and/or Apl. In one embodiment of the invention the control contains no *Anaplasma* sp. polypeptides or antibodies specific for *Anaplasma* sp. In one embodiment of the invention an antibody is specific for Aph antigens only. In another embodiment of the invention an antibody is specific for both Aph and Apl antigens. In another embodiment of the invention an antibody is specific for Apl antigens only. Alternatively, a polypeptide of the invention can be contacted with a test sample. Antibodies specific for Apl, and/or Aph in a positive test sample will form antigen-antibody complexes under suitable conditions. The amount of antibody-antigen complexes can be determined by methods known in the art.

In one embodiment of the invention, *Anaplasma phagocytophilum* and/or *Anaplasma platys* infection can be detected in a subject. A biological sample is obtained from the subject. One or more purified polypeptides comprising SEQ ID NOs: 1-21 or other polypeptides of the invention are contacted with the biological sample under conditions that allow polypeptide/antibody complexes to form. The polypeptide/antibody complexes are detected. The detection of the polypeptide/antibody complexes is an indication that the mammal has an *Anaplasma phagocytophilum* and/or *Anaplasma platys* infection. The lack of detection of the polypeptide/antibody complexes is an indication that the mammal does not have an *Anaplasma phagocytophilum* infection or an *Anaplasma platys* infection.

Because SEQ ID NOs:2, 3, 10, 13, 14, and 21 are specific for both anti-Apl and anti-Aph antibodies, the detected infection can be Aph infection, Apl infection, or both Apl and Aph infection. Because SEQ ID NOs:1, 4, 5, 6, 7, 9, 11, 12, 15, 16, 17, 18, and 20 are specific for anti-Aph antibodies, the detected infection is an Aph infection. Because SEQ ID NO:8 and 19 are specific for anti-Apl antibodies, the detected infection is an Apl infection. The lack of detection of polypeptide/antibody complexes is an indication that the subject does not have an *Anaplasma phagocytophilum* or an *Anaplasma platys* infection.

In one embodiment of the invention, Apl and/or Aph infection can be detected in a subject by about 5 days, 6 days, 7 days, 8 days, 9 days, 10 days, 11 days, 12 days, 13 days, 14 days, 15 days, 16 days, 17 days, 18 days, 19 days, 20 days, 21 days or more after the subject acquired the Apl and/or Apl infection. In one embodiment of the invention, Apl and/or Aph infection can be detected in a subject by about 21 days, 20 days, 19 days, 18 days, 17 days, 16 days, 15 days, 14 days, 13 days, 12 days, 11 days, 10 days, 9 days, 8 days, 7 days, 6 days, 5 days, or less after the subject acquired the Apl and/or Apl infection.

In one embodiment of the invention, the polypeptide/antibody complex is detected when an indicator reagent, such as an enzyme conjugate, which is bound to the antibody, catalyzes a detectable reaction. Optionally, an indicator reagent comprising a signal generating compound can be applied to the polypeptide/antibody complex under conditions that allow formation of a polypeptide/antibody/indicator complex. The polypeptide/antibody/indicator complex is detected. Optionally, the polypeptide or antibody can be labeled with an indicator reagent prior to the formation of a polypeptide/antibody complex. The method can optionally comprise a positive or negative control.

In one embodiment of the invention, one or more antibodies of the invention are attached to a solid phase or substrate. A test sample potentially comprising a protein comprising a polypeptide of the invention is added to the substrate. One or more antibodies that specifically bind polypeptides of the invention are added. The antibodies can be the same antibodies used on the solid phase or can be from a different source or species and can be linked to an indicator reagent, such as an enzyme conjugate. Wash steps can be performed prior to each addition. A chromophore or enzyme substrate is added and color is allowed to develop. The color reaction is stopped and the color can be quantified using, for example, a spectrophotometer.

In another embodiment of the invention, one or more antibodies of the invention are attached to a solid phase or substrate. A test sample potentially comprising a protein comprising a polypeptide of the invention is added to the substrate. Second anti-species antibodies that specifically bind polypeptides of the invention are added. These second antibodies are from a different species than the solid phase antibodies. Third anti-species antibodies are added that specifically bind the second antibodies and that do not specifically bind the solid phase antibodies are added. The third antibodies can comprise an indicator reagent such as an enzyme conjugate. Wash steps can be performed prior to each addition. A chromophore or enzyme substrate is added and color is allowed to develop. The color reaction is stopped and the color can be quantified using, for example, a spectrophotometer.

Assays of the invention include, but are not limited to those based on competition, direct reaction or sandwich-type assays, including, but not limited to enzyme linked immunosorbent assay (ELISA), western blot, IFA, radioimmunoassay (RIA), hemagglutination (HA), fluorescence polarization immunoassay (FPIA), and microtiter plate assays (any assay done in one or more wells of a microtiter plate). One assay of the invention comprises a reversible flow chromatographic binding assay, for example a SNAP® assay. See U.S. Pat. No. 5,726,010.

Assays can use solid phases or substrates or can be performed by immunoprecipitation or any other methods that do not utilize solid phases. Where a solid phase or substrate is used, one or more polypeptides of the invention are directly or indirectly attached to a solid support or a substrate such as a microtiter well, magnetic bead, non-magnetic bead, column, matrix, membrane, fibrous mat composed of synthetic or natural fibers (e.g., glass or cellulose-based materials or thermoplastic polymers, such as, polyethylene, polypropylene, or polyester), sintered structure composed of particulate materials (e.g., glass or various thermoplastic polymers), or cast membrane film composed of nitrocellulose, nylon, polysulfone or the like (generally synthetic in nature). In one embodiment of the invention a substrate is sintered, fine particles of polyethylene, commonly known as porous polyethylene, for example, 10-15 micron porous polyethylene from Chromex Corporation (Albuquerque, N. Mex.). All of these substrate materials can be used in suitable shapes, such as films, sheets, or plates, or they may be coated onto or bonded or laminated to appropriate inert carriers, such as paper, glass, plastic films, or fabrics. Suitable methods for immobilizing peptides on solid phases include ionic, hydrophobic, covalent interactions and the like.

In one type of assay format, one or more polypeptides can be coated on a solid phase or substrate. A test sample suspected of containing an anti-Apl, and/or anti-Aph antibody or antigen-binding fragment thereof is incubated with an indicator reagent comprising a signal generating compound conjugated to an antibody or antigen-binding antibody fragment specific for Apl and/or Aph for a time and under conditions sufficient to form antigen/antibody complexes of either antibodies of the test sample to the polypeptides of the solid phase or the indicator reagent compound conjugated to an antibody specific for Apl and/or Aph to the polypeptides of the solid phase. The reduction in binding of the indicator reagent conjugated to an anti-Apl and/or anti-Aph antibody to the solid phase can be quantitatively measured. A measurable reduction in the signal compared to the signal generated from a confirmed negative Apl and/or confirmed negative Aph test sample indicates the presence of anti-Apl and/or anti-Aph antibody in the test sample. This type of assay can quantitate the amount of anti-Apl and/or anti-Aph antibodies in a test sample.

In another type of assay format, one or more polypeptides of the invention are coated onto a support or substrate. A polypeptide of the invention is conjugated to an indicator reagent and added to a test sample. This mixture is applied to the support or substrate. If antibodies specific for Apl and/or Aph are present in the test sample they will bind the one or more polypeptides conjugated to an indicator reagent and to the one or more polypeptides immobilized on the support. The polypeptide/antibody/indicator complex can then be detected. This type of assay can quantitate the amount of anti-Apl, and/or anti-Aph antibodies in a test sample.

In another type of assay format, one or more polypeptides of the invention are coated onto a support or substrate. The test sample is applied to the support or substrate and incubated. Unbound components from the sample are washed away by washing the solid support with a wash solution. If Apl-specific, and/or Aph-specific antibodies are present in the test sample, they will bind to the polypeptide coated on the solid phase. This polypeptide/antibody complex can be detected using a second species-specific antibody that is conjugated to an indicator reagent. The polypeptide/antibody/anti-species antibody indicator complex can then be detected. This type of assay can quantitate the amount of anti-Apl and/or anti-Aph antibodies in a test sample.

The formation of a polypeptide/antibody complex or a polypeptide/antibody/indicator complex can be detected by e.g., radiometric, colorimetric, fluorometric, size-separation, or precipitation methods. Optionally, detection of a polypeptide/antibody complex is by the addition of a secondary antibody that is coupled to an indicator reagent comprising a signal generating compound. Indicator reagents comprising signal generating compounds (labels) associated with a polypeptide/antibody complex can be detected using the methods described above and include chromogenic agents, catalysts such as enzyme conjugates fluorescent compounds such as fluorescein and rhodamine, chemiluminescent compounds such as dioxetanes, acridiniums, phenanthridiniums, ruthenium, and luminol, radioactive elements, direct visual labels, as well as cofactors, inhibitors, magnetic particles, and the like. Examples of enzyme conjugates include alkaline phosphatase, horseradish peroxidase, beta-galactosidase, and the like. The selection of a particular label is not critical, but it will be capable of producing a signal either by itself or in conjunction with one or more additional substances.

Formation of the complex is indicative of the presence of anti-Apl and/or anti-Aph antibodies in a test sample. Therefore, the methods of the invention can be used to diagnose Apl and/or Aph infection in a patient.

The methods of the invention can also indicate the amount or quantity of anti-Apl and/or anti-Aph antibodies in a test sample. With many indicator reagents, such as enzyme conjugates, the amount of antibody present is proportional to the signal generated. Depending upon the type of test sample, it can be diluted with a suitable buffer reagent, concentrated, or contacted with a solid phase without any manipulation. For example, it usually is preferred to test serum or plasma samples that previously have been diluted, or concentrated specimens such as urine, in order to determine the presence and/or amount of antibody present.

The invention further comprises assay kits (e.g., articles of manufacture) for detecting anti-Apl and/or anti-Aph antibodies or antibody fragments, Apl polypeptides, and/or Aph polypeptides in a sample. A kit comprises one or more polypeptides of the invention and means for determining binding of the polypeptide to anti-Apl antibodies and/or or anti-Aph antibodies or antigen-binding antibody fragments in the sample. A kit or article of manufacture can also comprise one or more antibodies or antigen-binding antibody fragments of the invention and means for determining binding of the antibodies or antigen-binding antibody fragments to Apl polypeptides, and/or Aph polypeptides in the sample. A kit can comprise a device containing one or more polypeptides or antibodies of the invention and instructions for use of the one or more polypeptides or antibodies for, e.g., the identification of Apl and/or Aph infection in a mammal. The kit can also comprise packaging material comprising a label that indicates that the one or more polypeptides or antibodies of the kit can be used for the identification of Apl and/or Aph infection. Other components such as buffers, controls, and the like, known to those of ordinary skill in art, can be included in such test kits. The polypeptides, antibodies, assays, and kits of the invention are useful, for example, in the diagnosis of individual cases of Apl and/or Aph infection in a patient, as well as epidemiological studies of Apl and/or Aph outbreaks.

Polypeptides and assays of the invention can be combined with other polypeptides or assays to detect the presence of *Anaplasma* along with other organisms. For example, polypeptides and assays of the invention can be combined with reagents that detect heartworm and/or *Borrelia burgdorferi* and/or *Ehrlichia canis*.

Polynucleotides of the invention can be used to detect the presence of Apl and/or Aph polynucleotides in a sample. The polynucleotides can be used to detect Apl and/or Aph polynucleotides in a sample by a simple hybridization reaction and can also be used in, e.g., polymerase chain reactions (PCR) such as a real-time PCR reaction. Methods and compositions of the invention can also be used to differentially detect the presence Aph from other *Anaplasma* sp., such as Apl.

PCR assays are well described in the art, including, for example, U.S. Pat. Nos. 4,683,195; 4,683,202; 4,965,188. Generally, polynucleotide primers are annealed to denatured strands of a target nucleic acid. Primer extension products are formed by polymerization of deoxynucleoside triphosphates by a polymerase. PCR then involves repetitive cycles of template nucleic acid denaturation, primer annealing and extension of the annealed primers by the action of a thermostable polymerase. The process results in exponential amplification of the target *Anaplasma* sp. nucleic acids in the test sample, which allows for the detection of target polynucleotides existing in very low concentrations in a sample.

Real-time PCR assays are based on the detection of a signal, e.g., a fluorescent reporter signal. This signal increases in direct proportion to the amount of PCR product in a reaction. Real-time PCR is any amplification technique that makes it possible to monitor the evolution of an ongoing amplification reaction. See, Quantitation of DNA/RNA Using Real-Time PCR Detection, Perkin Elmer Applied Biosystems (1999); PCR Protocols (Academic Press New York, 1989). By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

One embodiment of the invention provides a method for detecting and/or quantifying Apl and/or Aph polynucleotides in a test sample. Sense primers and antisense primers can be added to a test sample under conditions suitable for a polymerase chain reaction. The primers hybridize with Apl and/or Aph polynucleotides such that an amplification product is formed if Apl and/or Aph polynucleotides are present in the test sample. Amplification products are detected and the presence and/or quantity of Apl and/or Aph polynucleotides is determined. Amplification products can be detected with a polynucleotide probe that hybridizes, under conditions suitable for a polymerase chain reaction, with an Apl and/or Aph polynucleotide sequence. The amplification product can be quantified by measuring a detection signal from the probe and comparing said detection signal to a second probe detection signal from a quantification standard. The quantification standard can be extracted in parallel with the test sample.

One embodiment of the invention provides a method for differentially detecting *Anaplasma phagocytophilum* from *Anaplasma platys* polypeptides in a sample. The method comprises:
  (a) contacting one or more antibodies that specifically bind to a polypeptide consisting of SEQ ID NOs:1, 4, 5, 6, 7, 9, 11, 12, 15, 16, 17, 18, or 20 with a sample under conditions that allow polypeptide/antibody complexes to form and detecting the polypeptide/antibody complexes; and
  (b) contacting one or more antibodies that specifically bind to a polypeptide consisting of SEQ ID NO:8 or 19 with the sample under conditions that allow polypeptide/antibody complexes to form and detecting the polypeptide/antibody complexes.

If the polypeptide/antibody complexes are detected in step (a) and in step (b) then the sample contains *Anaplasma phagocytophilum* polypeptides and contains *Anaplasma platys* polypeptides. If the polypeptide/antibody complexes are detected in step (a) and are not detected in step (b) then the sample contains *Anaplasma phagocytophilum* polypeptides and does not contain *Anaplasma platys* polypeptides. If the polypeptide/antibody complexes are not detected in step (a) and are detected in step (b) then the sample contains *Anaplasma platys* polypeptides and does not contain *Anaplasma phagocytophilum* polypeptides. If the polypeptide complexes are not detected in step (a) and are not detected in step (b) then the sample does not contain *Anaplasma platys* polypeptides and does not contain *Anaplasma phagocytophilum* polypeptides.

Another embodiment of the invention provides a method of detecting antibodies that specifically bind an *Anaplasma platys* polypeptide, an *Anaplasma phagocytophilum* polypeptide, or both an *Anaplasma platys* polypeptide and an *Anaplasma phagocytophilum* polypeptide. The method comprises:
 (a) contacting one or more purified polypeptides comprising SEQ ID NOs:1, 4, 5, 6, 7, 9, 11, 12, 15, 16, 17, 18, or 20 with a test sample, under conditions that allow polypeptide/antibody complexes to form and detecting the polypeptide/antibody complexes; and
 (b) contacting one or more purified polypeptides comprising SEQ ID NO:8 or 19, wherein the purified polypeptide with a test sample, under conditions that allow polypeptide/antibody complexes to form and detecting the polypeptide/antibody complexes.

If the polypeptide/antibody complexes are detected in step (a) and in step (b) then the sample contains antibodies the specifically bind *Anaplasma phagocytophilum* polypeptides and *Anaplasma platys* polypeptides (that is, antibodies that are capable of specifically binding both *Anaplasma platys* and *Anaplasma phagocytophilum* polypeptides). If the polypeptide/antibody complexes are detected in step (a) and are not detected in step (b) then the sample contains antibodies that specifically bind *Anaplasma phagocytophilum* polypeptides and does not contain antibodies that specifically bind *Anaplasma platys* polypeptides. If the polypeptide/antibody complexes are not detected in step (a) and are detected in step (b) then the sample contains antibodies that specifically bind *Anaplasma platys* polypeptides and does not contain antibodies that specifically bind *Anaplasma phagocytophilum* polypeptides. If the polypeptide complexes are not detected in step (a) and are not detected in step (b) then the sample does not contain antibodies specific for *Anaplasma platys* polypeptides and does not contain antibodies specific for *Anaplasma phagocytophilum* polypeptides.

Methods of Treatment, Amelioration, or Prevention of a Disease Caused by Aph and/or Apl Polypeptides, polynucleotides, and antibodies of the invention can be used to treat, ameliorate, or prevent a disease caused by Apl and/or Aph. For example, an antibody, such as a monoclonal antibody of the invention or antigen-binding fragments thereof, can be administered to an animal, such as a human or dog. In one embodiment of the invention an antibody or antigen-binding fragment thereof is administered to an animal in a pharmaceutical composition comprising a pharmaceutically acceptable carrier. A pharmaceutical composition comprises a therapeutically effective amount of an antibody or antigen-binding fragments thereof. A therapeutically effective amount is an amount effective in alleviating the symptoms of an Apl and/or Aph infection or in reducing the amount of Apl and/or Aph organisms in a subject.

Polypeptides or polynucleotides of the invention can be present in an immunogenic composition and used to elicit an immune response in a host. An immunogenic composition or immunogen is capable of inducing an immune response in an animal. An immunogenic polypeptide or polynucleotide composition of the invention is particularly useful in sensitizing an immune system of an animal such that, as one result, an immune response is produced that ameliorates or prevents the effect of Apl and/or Aph infection. The elicitation of an immune response in animal model can be useful to determine, for example, optimal doses or administration routes. Elicitation of an immune response can also be used to treat, prevent, or ameliorate a disease or infection caused by Apl and/or Aph. An immune response includes humoral immune responses or cell mediated immune responses, or a combination thereof. An immune response can also comprise the promotion of a generalized host response, e.g., by promoting the production of defensins.

One embodiment of the invention provides an immunogen that comprises a polypeptide of the invention and one or more additional regions or moieties covalently joined to the polypeptide at the carboxyl terminus or amino terminus. Each region or moiety can, for example, enhance the immune response, facilitate purification of the immunogen, or facilitate polypeptide stability.

The generation of an antibody titer by an animal against Apl and/or Aph can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to Apl and/or Aph can be identified by eliciting antibodies directed against Apl and/or Aph polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents and veterinarily acceptable carries and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $Alk(SO_4)_2$; $AlNa(SO_4)_2$, $AlNH_4(SO_4)$, Silica, Alum, $Al(OH)_3$, and $Ca_3(PO_4)_2$), polynucleotides (i.e. Poly IC and Poly AU acids), and certain natural substances (e.g. wax D from *Mycobacterium tuberculosis*, as well as substances found in *Corynebacterium parvum*, *Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® 80 (polysorbate) emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a mammal, such as a baboon, chimpanzee, dog, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a mammal at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with Apl and/or Aph or can be administered to an Apl and/or Aph-infected animal. An immunologically effective amount or therapeutically effective amount means the administration of that amount to an individual, either in a single dose or as part of series, is effective for treatment, amelioration, or prevention of Apl and or Aph infection. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

All patents, patent applications, and other scientific or technical writings referred to anywhere herein are incorporated by reference herein in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Detection of Anti-Aph and Anti-Apl Antibodies with Polypeptides Derived from the Aph p44 Protein Polypeptides shown in SEQ ID NOs:12-18 and 10 were coated at 0.5 m/mL on Immulon® 4 microtiter plates in carbonate buffer pH 9.6, overnight. For all examples, the polypeptide shown in SEQ ID NO:10 has an N at position 143, an A at position 145, and an I at position 156.

The plates were washed twice with PetChek® wash buffer. The plates were blocked with 2% TWEEN® 20 (polysorbate)/2.5% sucrose in 0.1M Tris pH 7.6, 2 h and then dried with desiccant overnight. A 1:200 dilution of test samples in conjugate diluent were added to the plates and incubated for 40 minutes. The plates were washed 6 times with PetChek® wash buffer. HRP-conjugated rabbit anti-dog IgG (H+ L) (Jackson ImmunoResearch Laboratories, Inc., West Grove, Pa.; Cat. No. 304-035-003), diluted 1:2000 in conjugate diluent, was added to the plates and incubated for 40 minutes. The plates were washed 6 times with PetChek® wash buffer. 60 µl of 3,3',5,5'-tetramethylbenzidine ("TMB") was added to the plates and incubated for 10 minutes. 50 µl of Stop solution was added and the A650 was determined. Test samples were as follows:

APL_13DPI: Apl experimentally infected dog 13 days post infection
APL_78DPI Apl experimentally infected dog 78 days post infection
APH: pool of samples from 7 Aph infected dogs from Minnesota
neg: pool of samples from 7 random healthy dogs The results are shown in Table 1 and FIG. 1.

TABLE 1

| Peptide | SEQ ID NO: | APL_13DPI | APL_78DPI | APH | neg |
|---|---|---|---|---|---|
| Aph rp44 | 10 | 1.13 | 0.49 | 2.62 | 0.13 |
| Aph p44-1 | 12 | 0.29 | 0.24 | 1.09 | 0.28 |
| Aph p44-2 | 13 | 1.40 | 1.57 | 3.42 | 0.22 |
| Aph p44-3 | 14 | 1.10 | 0.51 | 2.39 | 0.24 |
| Aph p44-4 | 15 | 0.22 | 0.16 | 3.08 | 0.18 |
| Aph p44-4-1 | 16 | 0.20 | 0.14 | 2.80 | 0.11 |
| Aph p44-4-2 | 17 | 0.19 | 0.14 | 2.38 | 0.11 |
| Aph p44-4-3 | 18 | 0.23 | 0.16 | 2.75 | 0.15 |

All 8 tested peptides showed positive reactivity to the pool of sera from 7 Aph infected dogs from Minnesota. rp44, p44-2, and p44-3 showed cross reactivity to the sera of an experimentally Apl infected dog at 2 different time points of infection. Reactivities of p44-1, p44-4, p44-4-1, p44-4-2, and p44-4-3 with the sera of the experimentally Apl infected dog were near background levels. Therefore, polypeptides p44-1, p44-4, p44-4-1, p44-4-2, and p44-4-3 are not cross-reactive to sera from Apl-infected dogs.

Example 2

Species Specific Detection of Aph or Apl in Field Samples from Endemic Areas

Polypeptides (Aph p44-4 and Apl p44-4 at 0.5 µg/mL; Aph rp44 at 0.25 µg/mL) were coated on Immulon® 4 plates in carbonate buffer pH 9.6, overnight. The plates were washed 2× with PetChek® wash buffer and then blocked with 2% TWEEN® 20 (polysorbate)/2.5% Sucrose in 0.1M Tris pH 7.6 for 2 hours. The plates were dried with desiccant overnight. A 25 µL test sample was mixed with 50 µL peptide:HRP conjugate (0.5 µg/mL for the p44-4-Aph (SEQ ID NO:15):HRP conjugate, 1 µg/mL for the p44-4-Apl (SEQ ID NO:19):HRP conjugate, and 3 µg/mL for Aph rp44 conjugate) and incubated on the microtiter plate (incubation time was 1 hour in the experiment shown in FIGS. 2, and 1 hour 45 minutes in the experiment shown in FIG. 3. The plates were washed 6 times with PetChek® wash buffer. 60 µl of TMB was added to the plates and incubated for 10 minutes. 50 µl of Stop solution was added and the A650 was determined. The cut off value was determined based on reactivities to 10 negative samples; cutoff=mean+2×SD (standard deviations).

FIG. 2 demonstrates the results using A. platys positive samples from dogs living in A. platys endemic areas (HP: Arizona, P: Bahamas). rp44 (SEQ ID NO:10) provided positive results for 4 of the 5 "HP" samples, and positive results for 7 of the 7 "P" samples. Aph p44-4 (SEQ ID NO:15) provided positive results for 0 of the 5 "HP" samples, and for 0 of the 7 "P" samples. Apl p44-4 (SEQ ID NO:19) provided positive results for 5 of the 5 "HP" samples, and 7 of the 7 "P" samples. Therefore, Aph p44-4 does not cross-react with sera from Apl infected dogs.

FIG. 3 demonstrates the results using A. phagocytophilum positive samples from dogs living in an Aph endemic area (Minnesota "ME"). rp44 (SEQ ID NO:10) provided strong positive results for 21 of the 22 ME samples. Aph p44-4 (SEQ ID NO:15) provided strong positive results for 20 of the 22 ME samples. Apl p44-4 (SEQ ID NO:19) provided negative results for 18 of the 22 samples and very weak positive results for 4 of the 22 ME samples. Therefore, Apl p44-4 can be considered to not cross-react with sera from Aph infected dogs.

Example 3

Time Course Response in an Apl Experimental Infection Model

Polypeptides (Aph p44-4 and Apl p44-4 at 0.5 µg/mL; Aph rp44 at 0.25 µg/mL) were coated on Immulon® 4 microtiter plates in carbonate buffer pH 9.6, overnight. The plates were washed 3 times with PetChek® wash buffer. The plates were blocked with 2% TWEEN® 20 (polysorbate)/2.5% sucrose in 0.1M Tris pH 7.6, 2 h and left to dry overnight. A 25 µL test sample was mixed with 50 µL peptide:HRP conjugate (0.5 µg/mL for Aph p44-4 conjugate, 1 µg/mL for Apl p44-4 conjugate, and 3 µg/mL for Aph rp44 conjugate) and incubated on the microtiter plate for 1 hour. The plates were washed 6 times with PetChek® wash buffer. 60 µl of TMB was added and allowed to incubate for 10 minutes. 50 µl of Stop solution was added and the A650 was determined. The results are shown in FIG. 4.

The results demonstrate that SEQ ID NO:19 (Apl p44-4) can be used to detect Apl infections. SEQ ID NO:19 can detect Apl infection at about 10 days post-infection. Aph p44-4 (SEQ ID NO:15) shows no cross reactivity with sera from the Apl infected dogs. Aph rp44 (SEQ ID NO:10) cross reacts with sera from the Apl infected dogs at about 14 days and can be used to detect Apl and Aph infection.

Example 4

Time Course Response in an Aph Experimental Infection Model

Aph p44-4 (SEQ ID NO:15) and Aph rp44 (SEQ ID NO:10) were tested for their reactivity with sera from experimentally Aph-infected dogs at a series of time points. 11 random healthy field dog samples were also tested. The polypeptides were coated on Immulon® 4 microtiter plates (Aph p44-4 at 0.5 µg/mL; Aph rp44 at 0.25 µg/mL) in carbonate buffer pH 9.6, overnight. The plates were washed four times with PetChek® wash buffer. The plates were blocked with 2% TWEEN® 20 (polysorbate)/2.5% Sucrose in 0.1M Tris pH 7.6, for 2 hours and then dried with desiccant overnight. A 25 µL test sample was mixed with 50 µL peptide:HRP conjugate (0.5 µg/mL for the p44-4-Aph (SEQ ID NO:15):HRP conjugate, and 3 µg/mL for Aph rp44 conjugate) and added to the plates. The plates were incubated for 1 hour. The plates were washed 6 times with PetChek® wash buffer. TMB was added to the plates and incubated for 10 minutes. 50 µl of Stop solution was added and the A650 was determined. The results are shown in FIG. 5. Aph p44-4 (SEQ ID NO:15) was able to detect Aph infection at about 10 to 14 days post-infection. Aph rp44 (SEQ ID NO:10) was able to detect Aph infection at about 10 days post-infection.

Example 5

Detection of Acute Aph Infection

Polypeptides were coated at 0.5 µg/mL or 1.0 µg/mL on Immulon® 4 plates in carbonate buffer pH 9.6, overnight. The plates were washed 4 times with PetChek® wash buffer and then blocked with 2% TWEEN® 20 (polysorbate)/2.5% sucrose in 0.1M Tris pH 7.6 for 2 hours. The plates were dried with desiccant overnight. 100 µl of a test serum sample at 1:200 dilution in sample diluent was incubated for 45 minutes. The plates were washed 6 times with PetChek® wash buffer. 100 µl of HRP-conjugated rabbit anti-dog IgG (H+L) (Jackson ImmunoResearch Laboratories, Inc., West Grove, Pa.; Cat. No. 304-035-003) at 1:2000 dilution in sample diluent was added and incubated for 45 minutes. The plates were washed 6 times with PetChek® wash buffer. 60 µl of TMB was added to the plates and incubated for 10 minutes. 50 µl of Stop solution was added and the A650 was determined. Test samples were as follows:

Positive ("+") represents a pool of seven sera from late-stage Aph infected dogs Negative ("−") represents a pool of 7 random healthy dog serum samples VML8, VML14, VML21 and VML156 represent serum samples from four dogs that were IFA positive for Aph and had acute clinical signs of anaplasmosis. The results are shown in FIG. 6. Aph p44-4 reacted with the 4 sera. Aph p44-1 and Aph p44-2 did not react with the 4 sera, while Aph p44-3 weakly reacted with the 4 sera. Therefore, Aph p44-4 and Aph p44-3 can be used to detect Aph in subjects with acute clinical signs of anaplasmosis.

Example 6

Performance of Peptide p44-4-v

Aph p44-4-v (SEQ ID NO:20) was tested with the samples listed in Table 2.

TABLE 2

| Sample Name | Sample Composition |
| --- | --- |
| VML21 | dog with acute clinical signs of Aph infection, IFA positive for Aph |
| ILS73 | dog with acute clinical signs of Aph infection, IFA positive for Aph, morulae positive |
| APH | Aph experimental infection, 14 days post infection |
| APL | Apl experimental infection, 13 days post infection |
| +ve | pool of samples from 7 Aph infected dogs from Minnesota |
| −ve | pool of samples from 7 random healthy dogs |

Figures 7A, 7B:
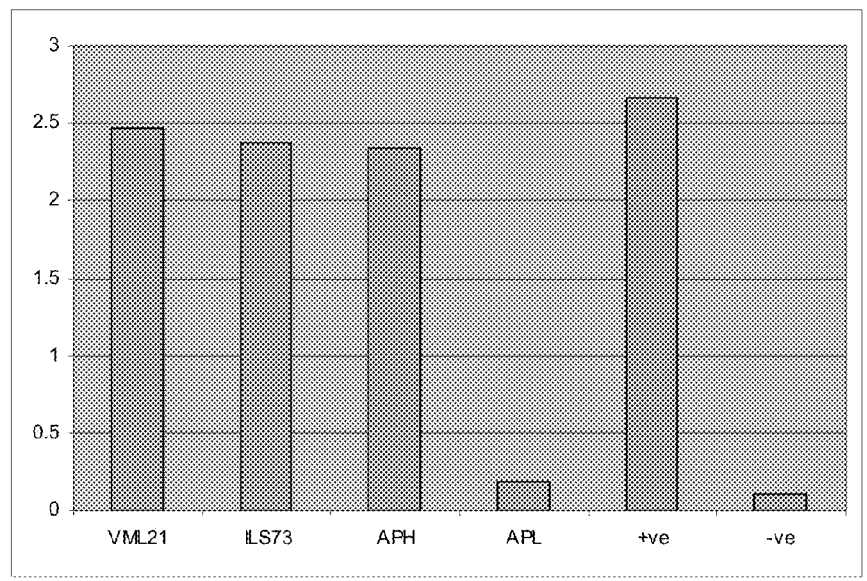
FIG. 7A-B shows the results of assays completed with polypeptides comprising SEQ ID NO:20.

Polypeptides were coated at 0.5 µg/mL on Immulon® 4 plates in carbonate buffer pH 9.6, overnight. The plates were washed 2 times with PetChek® wash buffer and then blocked with 2% TWEEN® 20 (polysorbate)/2.5% sucrose in 0.1M Tris pH 7.6 for 2 hours. The plates were dried with desiccant overnight. The test sample in a 1:200 dilution of conjugate diluent were added to the plates and incubated for 40 minutes. The plates were washed 6 times with PetChek® wash buffer. HRP conjugated rabbit anti-dog IgG (H+L) (Jackson ImmunoResearch Laboratories, Inc., West Grove, Pa.; Cat. No. 304-035-003) in a 1:2000 dilution of conjugate diluent was added to the plates and incubated for 40 minutes. The plates were washed 6 times with PetChek® wash buffer. 60 µl of TMB was added to the plates and incubated for 10 minutes. 50 µl of Stop solution was added and the A650 was determined. The results are shown in FIG. 7, and represent the average of duplicate experiments. p44-4-v provided positive results for the following samples: VML21; ILS73, APH, and +ve; and negative results for the following samples: APL and −ve. Therefore, Aph p44-4-v can detect Aph infection in acute cases, and at least as early as 14 days post-infection. Aph p44-4-v is not cross-reactive with sera from Apl infected dogs.

We claim:

1. A composition comprising one or more purified polypeptides, wherein the one or more polypeptides consist of an amino acid sequence set forth as SEQ ID NO:3 or 14, or consist of at least 30 contiguous amino acids of an amino acid sequence set forth as SEQ ID NOs:3 or 14, or consist of a polypeptide fragment having at least about 94% identity to any one of SEQ ID NOs:3 or 14 over the full length of SEQ ID NOs:3 or 14;

wherein, optionally, the one or more purified polypeptides are linked to an indicator reagent, a signal sequence, a stop transfer sequence, an amino acid spacer, a transmembrane domain, a protein purification ligand, a heterologous polypeptide, a moiety that enhances an immune response, a moiety that facilitates purification, a moiety that facilitates polypeptide stability, one or more additional polypeptides comprising any one of SEQ ID NOs:1-21 or a combination thereof.

2. A method of detecting antibodies that specifically bind an *Anaplasma phagocytophilum* polypeptide or an *Anaplasma platys* polypeptide or both in a test sample, comprising:

(a) contacting the composition of claim 1 with the test sample, under conditions that allow polypeptide/antibody complexes to form;

(b) detecting the polypeptide/antibody complexes;

wherein the detection of the polypeptide/antibody complexes is an indication that antibodies specific for an *Anaplasma phagocytophilum* polypeptide or an *Anaplasma platys* polypeptide or both are present in the test sample.

3. The method of claim 2, further comprising contacting the complexes of step (a) with an indicator reagent prior to the performance of step (b).

4. The method of claim 2, wherein the amount of antibodies in the test sample is determined.

5. The method of claim 2, wherein the one or more purified polypeptides are attached to a substrate.

6. The composition of claim 1, further comprising a pharmaceutically-acceptable or veterinarily acceptable carrier.

7. The composition of claim 6, further comprising an adjuvant.

8. A method of inducing an immune response in a mammal comprising administering an immunologically effective amount of the composition of claim 7 to the mammal.

9. The composition of claim 1, wherein the one or more purified polypeptides are attached to a solid support.

10. The composition of claim 1, wherein the one or more purified polypeptides are chemically synthesized.

* * * * *

SEQUENCE LISTING

```
<160> NUMBER OF SEQ ID NOS: 21

<210> SEQ ID NO 1
<211> LENGTH: 45
<212> TYPE: PRT
<213> ORGANISM: Artificial
<220> FEATURE:
<223> OTHER INFORMATION: Synthetic

<400> SEQUENCE: 1

Gly Ser Asp Val Arg Ala His Asp Val Ser Ala Leu Glu Thr Gly
1               5                   10                  15

Gly Ala Gly Tyr Phe Tyr Val Gly Leu Asp Tyr Ser Pro Ala Phe Ser
            20                  25                  30

Lys Ile Arg Asp Phe Ser Ile Arg Glu Ser Asn Gly Glu
        35                  40                  45

<210> SEQ ID NO 2
<211> LENGTH: 49
<212> TYPE: PRT
```

```
<213> ORGANISM: Artificial
<220> FEATURE:
<223> OTHER INFORMATION: Synthetic

<400> SEQUENCE: 2

Glu Ser Asn Gly Glu Thr Lys Ala Val Tyr Pro Tyr Leu Lys Asp Gly
1               5                   10                  15

Lys Ser Val Lys Leu Glu Ser His Lys Phe Asp Trp Asn Thr Pro Asp
            20                  25                  30

Pro Arg Ile Gly Phe Lys Asp Asn Met Leu Val Ala Met Glu Gly Ser
        35                  40                  45
Val

<210> SEQ ID NO 3
<211> LENGTH: 46
<212> TYPE: PRT
<213> ORGANISM: Artificial
<220> FEATURE:
<223> OTHER INFORMATION: Synthetic

<400> SEQUENCE: 3

Met Glu Gly Ser Val Gly Tyr Gly Ile Gly Ala Arg Val Glu Leu
1               5                   10                  15

Glu Ile Gly Tyr Glu Arg Phe Lys Thr Lys Gly Ile Arg Asp Ser Gly
            20                  25                  30

Ser Lys Glu Asp Glu Ala Asp Thr Val Tyr Leu Leu Ala Lys
        35                  40                  45

<210> SEQ ID NO 4
<211> LENGTH: 35
<212> TYPE: PRT
<213> ORGANISM: Artificial
<220> FEATURE:
<223> OTHER INFORMATION: Synthetic

<400> SEQUENCE: 4

Tyr Leu Leu Ala Lys Glu Leu Ala Tyr Asp Val Val Thr Gly Gln Thr
1               5                   10                  15

Asp Asn Leu Ala Ala Ala Leu Ala Lys Thr Ser Gly Lys Asp Ile Val
            20                  25                  30

Gln Phe Ala
        35

<210> SEQ ID NO 5
<211> LENGTH: 18
<212> TYPE: PRT
<213> ORGANISM: Artificial
<220> FEATURE:
<223> OTHER INFORMATION: Synthetic

<400> SEQUENCE: 5

Ala Lys Glu Leu Ala Tyr Asp Val Val Thr Gly Gln Thr Asp Asn Leu
1               5                   10                  15
Ala Ala

<210> SEQ ID NO 6
<211> LENGTH: 17
<212> TYPE: PRT
<213> ORGANISM: Artificial
<220> FEATURE:
<223> OTHER INFORMATION: Synthetic

<400> SEQUENCE: 6
```

```
Leu Ala Ala Ala Leu Ala Lys Thr Ser Gly Lys Asp Ile Val Gln Phe
1               5                   10                  15

Ala
```

```
<210> SEQ ID NO 7
<211> LENGTH: 20
<212> TYPE: PRT
<213> ORGANISM: Artificial
<220> FEATURE:
<223> OTHER INFORMATION: Synthetic

<400> SEQUENCE: 7

Val Val Thr Gly Gln Thr Asp Asn Leu Ala Ala Ala Leu Ala Lys Thr
1               5                   10                  15

Ser Gly Lys Asp
            20
```

```
<210> SEQ ID NO 8
<211> LENGTH: 32
<212> TYPE: PRT
<213> ORGANISM: Artificial
<220> FEATURE:
<223> OTHER INFORMATION: Synthetic

<400> SEQUENCE: 8

Ala Lys Lys Leu Pro His Thr Leu Val Ser Asp Gln Ser Asp Lys Phe
1               5                   10                  15

Leu Glu Glu Leu Lys Asn Thr Lys Ala Ala Glu Ile Val Lys Phe Ala
            20                  25                  30
```

```
<210> SEQ ID NO 9
<211> LENGTH: 35
<212> TYPE: PRT
<213> ORGANISM: Artificial
<220> FEATURE:
<223> OTHER INFORMATION: Synthetic

<400> SEQUENCE: 9

Tyr Leu Leu Ala Lys Glu Leu Ala Tyr Asp Val Val Thr Gly Gln Thr
1               5                   10                  15

Asp Lys Leu Thr Ala Ala Leu Ala Lys Thr Ser Gly Lys Asp Phe Val
            20                  25                  30

Gln Phe Ala
        35
```

```
<210> SEQ ID NO 10
<211> LENGTH: 213
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (143)..(143)
<223> OTHER INFORMATION: Xaa can be any naturally occurring amino acid
<220> FEATURE:
<221> NAME/KEY: misc_feature
<222> LOCATION: (145)..(145)
<223> OTHER INFORMATION: Xaa can be any naturally occurring amino acid
<220> FEATURE:
<221> NAME/KEY: misc_feature
<222> LOCATION: (156)..(156)
<223> OTHER INFORMATION: Xaa can be any naturally occurring amino acid

<400> SEQUENCE: 10

Gly Ser Asp Val Arg Ala His Asp Val Ser Ala Leu Glu Thr Gly
1               5                   10                  15
```

Gly Ala Gly Tyr Phe Tyr Val Gly Leu Asp Tyr Ser Pro Ala Phe Ser
            20                  25                  30

Lys Ile Arg Asp Phe Ser Ile Arg Glu Ser Asn Gly Glu Thr Lys Ala
        35                  40                  45

Val Tyr Pro Tyr Leu Lys Asp Gly Lys Ser Val Lys Leu Glu Ser His
    50                  55                  60

Lys Phe Asp Trp Asn Thr Pro Asp Pro Arg Ile Gly Phe Lys Asp Asn
65                  70                  75                  80

Met Leu Val Ala Met Glu Gly Ser Val Gly Tyr Gly Ile Gly Gly Ala
                85                  90                  95

Arg Val Glu Leu Glu Ile Gly Tyr Gly Arg Phe Lys Thr Lys Gly Ile
            100                 105                 110

Arg Asp Ser Gly Ser Lys Glu Asp Glu Ala Asp Thr Val Tyr Leu Leu
            115                 120                 125

Ala Lys Glu Leu Ala Tyr Asp Val Val Thr Gly Gln Thr Asp Xaa Leu
    130                 135                 140

Xaa Ala Ala Leu Ala Lys Thr Ser Gly Lys Asp Xaa Val Gln Phe Ala
145                 150                 155                 160

Asn Ala Val Lys Ile Ser Ser Pro Thr Ile Asp Gly Lys Val Cys Ser
                165                 170                 175

Gly Asp His Ala Ala Ile Val Ser Thr Lys Gly Lys Asp Tyr Lys Ala
            180                 185                 190

Asp Pro Lys Glu Ser Gly Asn Asn Gly His Glu Thr Ser Gln Cys Ser
            195                 200                 205

Gly Leu Ser Ser Ser
            210

<210> SEQ ID NO 11
<211> LENGTH: 35
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid

<400> SEQUENCE: 11

Tyr Leu Leu Ala Lys Glu Leu Ala Tyr Asp Val Val Thr Gly Gln Thr
1               5                   10                  15

Asp Xaa Leu Xaa Ala Ala Leu Ala Lys Thr Ser Gly Lys Asp Xaa Val
            20                  25                  30

Gln Phe Ala
        35

<210> SEQ ID NO 12
<211> LENGTH: 46
<212> TYPE: PRT
<213> ORGANISM: Artificial
<220> FEATURE:
<223> OTHER INFORMATION: Synthetic

<400> SEQUENCE: 12

-continued

```
Cys Gly Ser Asp Val Arg Ala His Asp Val Ser Ala Leu Glu Thr
1               5                  10                  15

Gly Gly Ala Gly Tyr Phe Tyr Val Gly Leu Asp Tyr Ser Pro Ala Phe
                20                  25                  30

Ser Lys Ile Arg Asp Phe Ser Ile Arg Glu Ser Asn Gly Glu
                35                  40                  45

<210> SEQ ID NO 13
<211> LENGTH: 45
<212> TYPE: PRT
<213> ORGANISM: Artificial
<220> FEATURE:
<223> OTHER INFORMATION: Synthetic

<400> SEQUENCE: 13

Cys Glu Ser Asn Gly Glu Thr Lys Ala Val Tyr Pro Tyr Leu Lys Asp
1               5                  10                  15

Gly Lys Ser Val Lys Leu Glu Ser His Lys Phe Asp Trp Asn Thr Pro
                20                  25                  30

Asp Pro Arg Ile Gly Phe Lys Asp Asn Met Leu Val Ala
                35                  40                  45

<210> SEQ ID NO 14
<211> LENGTH: 47
<212> TYPE: PRT
<213> ORGANISM: Artificial
<220> FEATURE:
<223> OTHER INFORMATION: Synthetic

<400> SEQUENCE: 14

Cys Met Glu Gly Ser Val Gly Tyr Gly Ile Gly Gly Ala Arg Val Glu
1               5                  10                  15

Leu Glu Ile Gly Tyr Glu Arg Phe Lys Thr Lys Gly Ile Arg Asp Ser
                20                  25                  30

Gly Ser Lys Glu Asp Glu Ala Asp Thr Val Tyr Leu Leu Ala Lys
                35                  40                  45

<210> SEQ ID NO 15
<211> LENGTH: 36
<212> TYPE: PRT
<213> ORGANISM: Artificial
<220> FEATURE:
<223> OTHER INFORMATION: Synthetic

<400> SEQUENCE: 15

Cys Tyr Leu Leu Ala Lys Glu Leu Ala Tyr Asp Val Val Thr Gly Gln
1               5                  10                  15

Thr Asp Asn Leu Ala Ala Ala Leu Ala Lys Thr Ser Gly Lys Asp Ile
                20                  25                  30

Val Gln Phe Ala
        35

<210> SEQ ID NO 16
<211> LENGTH: 19
<212> TYPE: PRT
<213> ORGANISM: Artificial
<220> FEATURE:
<223> OTHER INFORMATION: Synthetic

<400> SEQUENCE: 16

Cys Ala Lys Glu Leu Ala Tyr Asp Val Val Thr Gly Gln Thr Asp Asn
1               5                  10                  15
```

```
<210> SEQ ID NO 17
<211> LENGTH: 18
<212> TYPE: PRT
<213> ORGANISM: Artificial
<220> FEATURE:
<223> OTHER INFORMATION: Synthetic

<400> SEQUENCE: 17

Cys Leu Ala Ala Ala Leu Ala Lys Thr Ser Gly Lys Asp Ile Val Gln
1               5                   10                  15

Phe Ala

<210> SEQ ID NO 18
<211> LENGTH: 21
<212> TYPE: PRT
<213> ORGANISM: Artificial
<220> FEATURE:
<223> OTHER INFORMATION: Synthetic

<400> SEQUENCE: 18

Cys Val Val Thr Gly Gln Thr Asp Asn Leu Ala Ala Leu Ala Lys
1               5                   10                  15

Thr Ser Gly Lys Asp
            20

<210> SEQ ID NO 19
<211> LENGTH: 33
<212> TYPE: PRT
<213> ORGANISM: Artificial
<220> FEATURE:
<223> OTHER INFORMATION: Synthetic

<400> SEQUENCE: 19

Cys Ala Lys Lys Leu Pro His Thr Leu Val Ser Asp Gln Ser Asp Lys
1               5                   10                  15

Phe Leu Glu Glu Leu Lys Asn Thr Lys Ala Ala Glu Ile Val Lys Phe
            20                  25                  30

Ala

<210> SEQ ID NO 20
<211> LENGTH: 36
<212> TYPE: PRT
<213> ORGANISM: Artificial
<220> FEATURE:
<223> OTHER INFORMATION: Synthetic

<400> SEQUENCE: 20

Cys Tyr Leu Leu Ala Lys Glu Leu Ala Tyr Asp Val Val Thr Gly Gln
1               5                   10                  15

Thr Asp Lys Leu Thr Ala Ala Leu Ala Lys Thr Ser Gly Lys Asp Phe
            20                  25                  30

Val Gln Phe Ala
        35

<210> SEQ ID NO 21
<211> LENGTH: 214
<212> TYPE: PRT
<213> ORGANISM: Artificial
<220> FEATURE:
<223> OTHER INFORMATION: Synthetic
<220> FEATURE:
<221> NAME/KEY: misc_feature
<222> LOCATION: (144)..(144)
```

-continued

```
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid

<400> SEQUENCE: 21

Cys Gly Ser Asp Val Arg Ala His Asp Asp Val Ser Ala Leu Glu Thr
1               5                   10                  15

Gly Gly Ala Gly Tyr Phe Tyr Val Gly Leu Asp Tyr Ser Pro Ala Phe
            20                  25                  30

Ser Lys Ile Arg Asp Phe Ser Ile Arg Glu Ser Asn Gly Glu Thr Lys
        35                  40                  45

Ala Val Tyr Pro Tyr Leu Lys Asp Gly Lys Ser Val Lys Leu Glu Ser
    50                  55                  60

His Lys Phe Asp Trp Asn Thr Pro Asp Pro Arg Ile Gly Phe Lys Asp
65                  70                  75                  80

Asn Met Leu Val Ala Met Glu Gly Ser Val Gly Tyr Gly Ile Gly Gly
                85                  90                  95

Ala Arg Val Glu Leu Glu Ile Gly Tyr Glu Arg Phe Lys Thr Lys Gly
            100                 105                 110

Ile Arg Asp Ser Gly Ser Lys Glu Asp Glu Ala Asp Thr Val Tyr Leu
        115                 120                 125

Leu Ala Lys Glu Leu Ala Tyr Asp Val Val Thr Gly Gln Thr Asp Xaa
        130                 135                 140

Leu Xaa Ala Ala Leu Ala Lys Thr Ser Gly Lys Asp Xaa Val Gln Phe
145                 150                 155                 160

Ala Asn Ala Val Lys Ile Ser Ser Pro Thr Ile Asp Gly Lys Val Cys
                165                 170                 175

Ser Gly Asp His Ala Ala Ile Val Ser Thr Lys Gly Lys Asp Tyr Lys
            180                 185                 190

Ala Asp Pro Lys Glu Ser Gly Asn Asn Gly His Glu Thr Ser Gln Cys
        195                 200                 205

Ser Gly Leu Ser Ser Ser
    210
```